(12) United States Patent
Kamalakaran et al.

(10) Patent No.: US 8,652,777 B2
(45) Date of Patent: Feb. 18, 2014

(54) METHOD FOR THE ANALYSIS OF OVARIAN CANCER DISORDERS

(75) Inventors: Sitharthan Kamalakaran, Pelham, NY (US); Robert Lucito, East Meadow, NY (US); James Bruce Hicks, Lattingtown, NY (US)

(73) Assignees: Koninklijke Philips N.V., Eindhoven (NL); Cold Spring Harbor Laboratories, Cold Spring Harbor, NY (US)

( * ) Notice: Subject to any disclaimer, the term of this patent is extended or adjusted under 35 U.S.C. 154(b) by 781 days.

(21) Appl. No.: 12/678,423

(22) PCT Filed: Sep. 16, 2008

(86) PCT No.: PCT/IB2008/053743
§ 371 (c)(1),
(2), (4) Date: Mar. 16, 2010

(87) PCT Pub. No.: WO2009/037633
PCT Pub. Date: Mar. 26, 2009

(65) Prior Publication Data
US 2010/0273674 A1    Oct. 28, 2010

Related U.S. Application Data

(60) Provisional application No. 60/972,839, filed on Sep. 17, 2007.

(51) Int. Cl.
*C12Q 1/68* (2006.01)
*C12P 19/34* (2006.01)

(52) U.S. Cl.
USPC .......................... 435/6.1; 435/91.1; 435/91.2

(58) Field of Classification Search
None
See application file for complete search history.

(56) References Cited

U.S. PATENT DOCUMENTS

| | | |
|---|---|---|
| 5,744,305 A | 4/1998 | Fodor |
| 5,837,832 A | 11/1998 | Chee |
| 6,265,171 B1 | 7/2001 | Herman |
| 2006/0292564 A1 | 12/2006 | Maier |
| 2007/0087365 A1 | 4/2007 | Van Criekinge |

FOREIGN PATENT DOCUMENTS

| | | |
|---|---|---|
| WO | 2005024055 A1 | 3/2005 |
| WO | 2006031831 A2 | 3/2006 |

OTHER PUBLICATIONS

Wei et al; Clinical Cancer Research, vol. 12, May 2006, pp. 2788-2794.*
Balch, C. et al "The Epigenetics of Ovarian Cancer Drug Resistance and Resensitization" American Journal of Obstetrics and Gynecology, vol. 191, No. 5, Nov. 1, 2004, pp. 1552-1557.
Wei, Susan H. et al "Prognostic DNA Methylation Biomarkers in Ovarian Cancer" Clinical Cancer Research: An Official Journal of the American Association for Cancer Research, May 1, 2006, vol. 12, No. 9, pp. 2788-2794.
Kikuchi, Ryoko et al "Promoter Hypermethylation Contributes to Frequent Inactivation of a Putative Conditional Tumor Suppressor Gene Connective Tissue Growth Factor in Ovarian Cancer" Cancer Research, American Association for Cancer Research, vol. 67, No. 15, Aug. 2007, p. 7095-7105.
Bolstad, B.M. et al "A Comparison of Normalization methods for High Density Oligonucleotide Array Data Baed on Variance and Bias" Bioinformatics, vol. 19, No. 2, 2003, pp. 185-193.
Rein, Theo et al "Identifying 5-Methylcytosine and related Modifications in DNA Genomes" Nucleic Acids Research, 1998, vol. 26, No. 10, pp. 2255-2264.
Mei, Rui et al "Probe Selectionfor High-Density Oligonucleotide Arrays" Proc. National Academy Science, Sep. 30, 2003, vol. 100, No. 20, pp. 11237-11242.
Lucito, Robert et al "Representational Oligonucleotide Microarray Analysis: A High-Resolution Method to Detect Genome Copy Number Variation" Genome Research, Sep. 2003, vol. 13, No. 10, pp. 2291-2305.

* cited by examiner

*Primary Examiner* — Jehanne Sitton

(57) ABSTRACT

The invention relates to a method for the analysis of ovarian cancer disorders, comprising determining the genomic methylation status of one or more CpG dinucleotides in a sequence selected from the group of sequences according to SEQ ID NO. 1 to 10 and/or SEQ ID NO. 50 to SEQ ID NO. 60. Optionally, additionally following steps are performed, the one or more results from the methylation status test is input into a classifier that is obtained from a Diagnostic Multi Variate Model, calculating a likelihood as to whether the sample is from a normal tissue or an ovarian cancer tissue and/or, calculating an associated p-value for the confidence in the prediction.

4 Claims, 3 Drawing Sheets

SEQUENCE LISTING

<160> NUMBER OF SEQ ID NOS: 91

<210> SEQ ID NO 1
<211> LENGTH: 118
<212> TYPE: DNA
<213> ORGANISM: Homo sapiens

<400> SEQUENCE: 1
gccctggcac cgtgagggga aagaggcgtc aggtgcctgg ctgaagcctg aaggtgaccc      60
gaaaacaagt cagagcccga gagatccacc cgcgcccgcg cggggggacca agggcccg     118

<210> SEQ ID NO 2

<211> LENGTH: 1517
<212> TYPE: DNA
<213> ORGANISM: Homo sapiens

<400> SEQUENCE: 2

| | | | | | |
|---|---|---|---|---|---|
| ggcctggcgc | aacgctgagc | agctggcgcg | tcccgcgcgg | ccccagttct | gcgcagcttc | 60 |
| ccgaggctcc | gcaccagccg | cgcttctgtc | cgcctgcagg | tagggagcgt | tgttcctccg | 120 |
| cgggtgccca | cggcccagta | tctctggcta | gctcgctggg | cactttagga | cggagggtct | 180 |
| ctacaccctt | tctttgggat | ggagagagga | gaagggaaag | ggaacgcgat | ggtctagggg | 240 |
| gcagtagagc | caattacctg | ttgggggttaa | taagaacagg | caatgcatct | ggccttcctc | 300 |
| caggcgcgat | tcagttttgc | tctaaaaata | atttatacct | ctaaaaataa | ataagatagg | 360 |
| tagtatagga | taggtagtca | ttcttatgcg | actgtgtgtt | cagaatatag | ctctgatgct | 420 |
| aggctggagg | tctggacacg | ggtccaagtc | caccgccagc | tgcttgctag | taacatgact | 480 |
| tgtgtaagtt | atcccagctg | cagcatctaa | gtaagtctct | tcctgcgcta | agcaggtcca | 540 |
| ggatccctga | acggaattta | tttgctctgt | ccattctgag | aacccaaagg | agtcctaaaa | 600 |
| gaggaatgga | ggagcctaag | aataaaaata | gtataataaa | acatttctta | gacacattga | 660 |
| ccttggccta | tgtcaaagtt | cagtctgggt | ttgtcttata | acacaaggag | taaaagtacc | 720 |
| attgttctac | ctctttttt | aatacttgaa | aaaaatttac | tgtggatgct | tttctatgaa | 780 |
| ttaaataacc | ttctaaaaaa | tgttttcatt | gctgcattcg | attagattgg | gtaactaaat | 840 |
| gaaattaatt | cctcactgtt | gggtataaag | gttatttaca | gtggttctgt | cttagccatt | 900 |
| cactgaactc | attgcatata | tatctctgga | atattgctga | ttgtttcctt | caagtaaact | 960 |
| tagaagtgta | actacttagt | caaagagcct | gaatattta | aaggccttt | gaagaaaact | 1020 |
| gaaaatgctt | tccagaaagg | atgtatcagt | tgacaatgac | agtcgtcaac | agtatttaag | 1080 |
| gagaactatg | atactctgaa | gaaaaactta | gcctttctca | gtaaaagtag | gtaggcagag | 1140 |
| gccacatgac | agcagttaga | gtgtggtctt | caaggaagtc | acagaaatac | tgtggggaat | 1200 |
| tgaaacccca | tgtggaaaat | gtacaagagt | gtctcagtgt | gactgagaag | gaggttgggc | 1260 |
| atggggtttc | atggagttta | ataaagtttg | gtcacttagt | agaggtttaa | taaatcaact | 1320 |
| gtcttaatct | ttgatcctac | ttaagaattt | ttttttgtt | tttgtagaga | tggggctctt | 1380 |
| gttatgttgc | ccaggctgtt | ctcgaactcc | tagcctcagg | cgatcctccc | tcctcaggct | 1440 |
| ccagaagtcc | tgggattact | ggcgggagcc | accatgcagg | cctcttgctc | ctacttttga | 1500 |
| gaaaggaagt | ttaaccg | | | | | 1517 |

<210> SEQ ID NO 3
<211> LENGTH: 968
<212> TYPE: DNA
<213> ORGANISM: Homo sapiens

<400> SEQUENCE: 3

| | | | | | |
|---|---|---|---|---|---|
| ggcccaccca | gggctcaagc | cctgaccccc | ctgggcccct | gggctgcccc | gccccgatag | 60 |
| gaattcattc | cgtcagccca | acgcagccaa | tcggggcggt | ccacgccagg | tggactgctg | 120 |
| tgccccgcgg | ggtcattagg | ttaattgcag | cctggacaca | ccccactgag | ttctaccgtt | 180 |
| ggccctccat | gtacccagct | tccacatctg | tggattccaa | aagacacaga | gagaatcttc | 240 |
| ttgggagtaa | aagcgaaaat | aacaacaccg | caagacagaa | tcgtaggaag | aagaaccaac | 300 |
| agaggatgac | aactctttac | ctggcattga | cgttgtgtga | ggggacttgg | aaacattggt | 360 |
| agaaaagtgg | gattaaggga | gaaagaggaa | aaaggcgtat | tttactcctc | aacctcggct | 420 |

| | |
|---|---|
| ccatcagcat caagacccctt ctggaagcag tgtcttttcc ccgccgtcta gcccatccct | 480 |
| taaagccccc agggtcctgg gaatttaact atttccatgc aatctttttt ccattgttaa | 540 |
| ctgaagaaaa ctgggtgccc cttacaggtt ttccaagaca aggaaacaaa gagaagtcag | 600 |
| caggcgccaa atcaggattg tcaggtggac gcctcacggt ttcccatggc aagtcttgcc | 660 |
| cagctgccct tgttcgaaga aaggcatgat caggaacact gtcgtggtgg agaagaagtc | 720 |
| tctggtgggg accttcttcg ctccagcttt ggctaacttt ctgaaaacgc tctgctagcg | 780 |
| agcagatgtg atcagggttt ggccctgcag aaagtcaacc agcagaatcc ctctagcatc | 840 |
| tccccccccc accccgcccc caacggtggc catgacctct gctcttgact gctcctctgc | 900 |
| agcttcgact ggagcactgc cacctcttgg tagccatggc ttcgtgcttg gtcttcagga | 960 |
| tcctgccg | 968 |

<210> SEQ ID NO 4
<211> LENGTH: 357
<212> TYPE: DNA
<213> ORGANISM: Homo sapiens

<400> SEQUENCE: 4

| | |
|---|---|
| gggcacaggc aagcggacga gccagttatc cctcagagct cctgctgcct cgcccgcttt | 60 |
| ctctcggaaa cgtgaagtgt ggcctcagct gaaagtgagg tgagcgtgag tgtggacatg | 120 |
| tgtcagtgtg cgtgtgcatg ggaggagtgt gtgtgcgctt gatgacgatg atggagccca | 180 |
| gtgagccacc gtccgtggag tgtcagagcc tcctaggatg ccacgccga aggtgcggaa | 240 |
| ggaggcggct ggcccagcgt cagacgtttc cagcatccgc gggagtgaaa cggaggctgg | 300 |
| tgggtggttg tgatgtgttt ctttaagaat ggatcctgca ggttcttctt cctcccg | 357 |

<210> SEQ ID NO 5
<211> LENGTH: 48
<212> TYPE: DNA
<213> ORGANISM: Homo sapiens

<400> SEQUENCE: 5

| | |
|---|---|
| gccccgcgct tggcgcccga ctcgcctcgt cccgaacaat gcatgccg | 48 |

<210> SEQ ID NO 6
<211> LENGTH: 792
<212> TYPE: DNA
<213> ORGANISM: Homo sapiens

<400> SEQUENCE: 6

| | |
|---|---|
| gctccgcagc ctccgcgcag tccgctcggc tctggcactt gcgggaggtg gtgacggcta | 60 |
| gccgtcgccg cccgcgccag aacttgcgtc tcctcccccg acctgcattg ggggagggg | 120 |
| accgagggcg gagctggggg cgtggggagg gaatgtctgg gatggtctgg tattgcacag | 180 |
| ccgaggaaca ccagagttcc ttctgggaag acgggctagg gagctcagtg gtctcaggtc | 240 |
| tggtttcaga gttccgcctc tgcgtgcctc agtttaccct ttcccccttt gcccaagggg | 300 |
| gcaaggtaga gcgctgtcgg ggattgggtt tcataatccc cttccacttg acctccccgc | 360 |
| cacacccact aatcttcagg aactcaagtt ctcgcttttc ccagacgcac gcaagaaccg | 420 |
| tgcaccatct cgctcgctct ctgcccgccc gcgccttaca ccttcccgc tcggccgcag | 480 |
| aaacagaaga tccaggagcg atgctctccc actgtcccct tcccgccc gcgcgcttcc | 540 |
| tttctcggtt cccactctga ctgggaaaca gaaaatcaac gcgcggcgcg gctgcaaagt | 600 |
| cggtttccta ttggtcagcg cctcctgggc tgagcccgcc cgccccgcct cttctcccac | 660 |

```
ctaggcgggg cctccccgca gaccccgac tgcctccagc ccgcagtccc accgcctgcc      720
aggagatctt aaaggggccg cggccgcaat cagacgctga gcggcgtggg gagggggtgg      780
ctcagtgacc cg                                                          792
```

<210> SEQ ID NO 7
<211> LENGTH: 955
<212> TYPE: DNA
<213> ORGANISM: Homo sapiens

<400> SEQUENCE: 7

```
gcccaggctt cggctctcag cttagggaga ttctgataat acgcagagcc caaggtgtgt       60
gtagttttaa caaaaagctt cccaagcgaa tctgatacac atctaggatt aagaaacact      120
gctttaaact aagaaaggac taactgcaga agttcagcca caagtcaacc agatgtatgc      180
ccttaacatt cacatgagca gttggctaaa gtctcttata aggctatttc tatttccgag      240
gtttcagaac gggtagttat agtctgaaat acaccccaga ggacagagtc aggtccaatc      300
ttttctgtaa gacaccttgc tcaagactgc tgtgaaggaa taagagagct gcagccaaag      360
atcatcccaa agtctcccag aacactctat cattatatcc atctcacatg aaatatgggt      420
gtgtacattt tttccttcac tagattggca agtattccag cgcagggcaa atctcttttt      480
tctcccacca aggaacacaa tatcccatac ataataggtg tttgacaggt ttttttttta      540
aattgaattg aatccttacc tagctcctag ggtctgacta tatataccca taaattatac      600
atctgtttat aaaacatttc aatcacacca agaacatat  atatggaaga aagaacgata      660
aacaagcacc catggaccca cccccccgtt tatgaaacag aactttgcca gtgctttcga      720
agttccttac tgaactagat cttttaaaaa cagcaacgat tttctgaatt ttaatcagaa      780
ggcatgcatt ccttcattca ttgattcgat tccgtcatgg tcagacccgc ctaccaagtg      840
tcaacatgat atacacgatg taagtattcc actgttgggg tgaggagggt caaaagtgac      900
aatatgctat ctccagagac tacggatcgc ctttgctgca atggtccca acccg           955
```

<210> SEQ ID NO 8
<211> LENGTH: 242
<212> TYPE: DNA
<213> ORGANISM: Homo sapiens

<400> SEQUENCE: 8

```
gcgacccaag aagagtaagc aaactaccgt ccacccagcg gatcaggtcc aatccctgcg       60
cctcggccca atccctagag ccccgcgcg ccgtatcccc tcccccccaa ctctggaccc      120
cgccgtctgt ccccgcggca tcaccagggt gctggagttt ccgagcagg ccccttgcgc      180 taagcgagag gatctgtgag ggaaagttgg gagagccact tctggctttt gtgaagatcc      240
cg                                                                    242
```

<210> SEQ ID NO 9
<211> LENGTH: 264
<212> TYPE: DNA
<213> ORGANISM: Homo sapiens

<400> SEQUENCE: 9

```
gaggtggggt ggggaagtgg cgctggagct cagcttcctg cttttatgct cggcggccac       60
cgtgatgcac acacactcga ggtccgccac cccgcagtgc cgtgcacccc tctgccccca      120
cctcggaatt tttgtgcccg agcgctcggg atccacggca aaaccaggca cattcctccc      180
tctgcagact caccgcctgg tttgtagaca ctggtctccg cctggggcgt caatagtttc      240
```
aggatttaaa gcagaaagac accg                                        264

<210> SEQ ID NO 10
<211> LENGTH: 248
<212> TYPE: DNA
<213> ORGANISM: Homo sapiens

<400> SEQUENCE: 10
gcctgctcag actaggttct gcccactctg accttctaaa tggtacgtgg gaggacgtcc    60
gtccccttcg gacccaagag tcaccgtaac actctagaag gggagaaaag gagcgagggc   120
ggcaggcgac agagaacctc gcgagtcagc ggccccgcgc agaccccccc aggcacggtc   180
ccctgcggcc acgtcggctg ctcggcgcct gcgcaatctc tttctctcca gcgaaaccga   240
ggcctccg                                                            248

<210> SEQ ID NO 11
<211> LENGTH: 62
<212> TYPE: DNA
<213> ORGANISM: Homo sapiens

<400> SEQUENCE: 11
ggagcctagt gccatgcagc agcggcggcg gtggcggctt cccaagcgcg gcggcaaatc    60
cg                                                                   62

<210> SEQ ID NO 12
<211> LENGTH: 117
<212> TYPE: DNA
<213> ORGANISM: Homo sapiens

<400> SEQUENCE: 12
gagggctcgg gaccagcgcg agcaccttcc ctggaagccc acatccatca cccagcgatc    60
tcctctccat cgagagcagg gcttgctgag agtggcggag gaccttgaag gctcccg      117

<210> SEQ ID NO 13
<211> LENGTH: 63
<212> TYPE: DNA
<213> ORGANISM: Homo sapiens

<400> SEQUENCE: 13
gggactgcag tcagctattt aaacctcccg cccacctttt ctttagaccc gcgtctcacc    60
ccg                                                                  63

<210> SEQ ID NO 14
<211> LENGTH: 62
<212> TYPE: DNA
<213> ORGANISM: Homo sapiens

<400> SEQUENCE: 14
gccgcatgag acgctcccgc ccattggccc gccgtatccg ccaccgccat tggcccgccc    60
cg                                                                   62

<210> SEQ ID NO 15
<211> LENGTH: 105
<212> TYPE: DNA
<213> ORGANISM: Homo sapiens

<400> SEQUENCE: 15
ggccaacctg agggtacggc gctggcggtg cgggtccctg ggcgggcgcg gcgggaatag    60
cggcctcggg gagatgcggt gcgaagggac cgagagggaa gcccg                  105

```
<210> SEQ ID NO 16
<211> LENGTH: 38
<212> TYPE: DNA
<213> ORGANISM: Homo sapiens

<400> SEQUENCE: 16 gtgtccccccc tccctctcat aacgttcccc gcacaccg                              38

<210> SEQ ID NO 17
<211> LENGTH: 441
<212> TYPE: DNA
<213> ORGANISM: Homo sapiens

<400> SEQUENCE: 17
ggggccacgt aatgctgagt gctgattggc tgctcttggc tcctcccctc atcccgcttt       60
tggcccaaga gcgtggtgca gattcacccg cgcgaggtag gcgctctggt gcttgcggag      120
gacgcttcct tcctcagatg caccgatctt cccgatactg cctttggagc ggctagattg      180
ctagccttgg ctgctccatt ggcctgcctt gccccttacc tgccgattgc atatgaactc      240
ttcttctgtc tgtacatcgt tgtcgtcgga gtcgtcgcga tcgtcgtggc gctcgtgtga      300
tggccttcgt ccgtttagag tagtgtagtt agttaggggc caacgaagaa gaaagaagac      360
gcgattagtg cagagatgct ggaggtggtc agttactaag ctagagtaag atagcggagc      420
gaaaagagcc aaacctagcc g                                                441

<210> SEQ ID NO 18
<211> LENGTH: 268
<212> TYPE: DNA
<213> ORGANISM: Homo sapiens

<400> SEQUENCE: 18
gaagtcaggc ccgagggagc tgggagggcg ttagcgaagc caggttcggt cgtggggtg       60 gggaagtgca ggagtggcgc gcggcgtact acatgtcccg tgagcctccg cggcgggacg     120 gggcgggggcc gcgggacgcc aggaggcgga ggcggagtgg agttaggtaa gagcgttacc    180
agccgtcttg tctgttgggc cgaggtcccc cttcaggggc gccctctggt gcgtcttttt     240
cactcagtgt ccttttgggg ggtccccg                                        268

<210> SEQ ID NO 19
<211> LENGTH: 266
<212> TYPE: DNA
<213> ORGANISM: Homo sapiens

<400> SEQUENCE: 19
gctgggctgc ggggcggggc ctggacggcc acgtgactcg cggggcgggg ccagagtccg      60
cggagggacg ggaggcgggg cctggactgc ctcgtgacca gtgggcgggg gcctgagcca     120
gctgtgtgcg gatggggcgg ggcttttggag gccgcgtgac cagcggcggg tcacgtgacg    180
cggtgcctgg cgccgagcct cccaagatgg cggtgtgcat cgcggtgatt gccaaggagg    240
tgcgtacgcg cggcgtgggg cgtccg                                          266

<210> SEQ ID NO 20
<211> LENGTH: 39
<212> TYPE: DNA
<213> ORGANISM: Homo sapiens

<400> SEQUENCE: 20
gtgagtgctt gccctccctg gttacctcgc cagtctccg                             39
```

<210> SEQ ID NO 21
<211> LENGTH: 250
<212> TYPE: DNA
<213> ORGANISM: Homo sapiens

<400> SEQUENCE: 21
gggatcagac gggaggtgga gttgcgcggg gagggcgggc gagtcgggcg cccgctctga      60
gagtcggttt cttttccccc tcttgcgtgg ggcggggtgg tgcgttccga gttcccagga     120
gttcgacgcg ggcgggtgcc gaggggaggg gagtggcggc ggcggcgggc ggctcccgct     180
tcagcctcgg cagtggcgtc ggcgacggcg tgtcgaggc agccgccagc gttcggccaa     240
gtgtcagccg                                                            250

<210> SEQ ID NO 22
<211> LENGTH: 156
<212> TYPE: DNA
<213> ORGANISM: Homo sapiens

<400> SEQUENCE: 22
ggaggtggag gttgcagtga accgagatcg tgccactgta ctccagtctg ggtgacagag      60
cgagactcca tctcaaaaaa acaaaaaaaa acgaaaaaaa aaaaaaagac ggacgtaccg     120
aagaacggcg gtaactcctc ccctcgagc cgcccg                                156

<210> SEQ ID NO 23
<211> LENGTH: 229
<212> TYPE: DNA
<213> ORGANISM: Homo sapiens

<400> SEQUENCE: 23
ggagagctgc agcgccatgg ccagggacac aaacaaaagc acgcgcttcc actccgcgga      60
cagcaaccac agcggctcca acagcacttc cccgccaagc gttcaaaag taacgacgca     120 gcacgtcgtc aggtccttg cgcaggcgcg acgagccttt aagcccagcc ccacgcagcg     180
gggacctgcc cttctctca gccttcctgt gatgtcgcgg gagcggccg                 229

<210> SEQ ID NO 24
<211> LENGTH: 187
<212> TYPE: DNA
<213> ORGANISM: Homo sapiens

<400> SEQUENCE: 24
gagccaacag gtgcggggtg tgggggaccc ccaggcctgg gatgggggtt ccaaaggacc      60
cgcggcgagg gatgggagga gccaagagtc tcgggggggta acctgggtgc tgggagactg     120
gctcctcggc cagcgctgct ctcctctagg caggctccga gtgccctcgc tccccgcgc     180 cttcccg                                                               187

<210> SEQ ID NO 25
<211> LENGTH: 324
<212> TYPE: DNA
<213> ORGANISM: Homo sapiens

<400> SEQUENCE: 25
gagcgaggcc agtgggttcc tcggtttggc ctgatcacac tggaggaggc cctgcttgcg      60
tcagtcttgg cgctagaacc cgagggcctg gagccgccag gggagacgcg gagctcggcc     120
gagacgaggt ggcttttggc acctctttac cctctggccc cagtgctgac tgggggaatag   180 tcgctttgac cgtgcaaaga gcattctagg cggggtgggg gggttctgct gtgtgtgcca     240

```
gtgttaggta ttgcccccat tgcttttaga aatatgccct gcatggtgaa tctccgtctc      300
tactaaaata caaaaattag gccg                                             324
```

<210> SEQ ID NO 26
<211> LENGTH: 61
<212> TYPE: DNA
<213> ORGANISM: Homo sapiens

<400> SEQUENCE: 26

```
gagagctgcg agccccgact ttctcgccag gctctccagt acattccgag gctccacccc       60
g                                                                       61
```

<210> SEQ ID NO 27
<211> LENGTH: 1124
<212> TYPE: DNA
<213> ORGANISM: Homo sapiens

<400> SEQUENCE: 27

```
gtatgaggcc acccttggtg ctgtctgtaa ttatctagac atggcagcca ggatccaaca       60
gctttgcgtt ttaactcata tggtcttttcc tggcgaattc cttgccccccc tctgctcccc     120 acttagcttg acttcctgtc ttttatcatc cgcaatctat caagatccta caatgtgctc      180
agtgtagggc ggaacaaatc actgttttac ctcacaattt aaggaaggca gggggctagt      240
ttttaagata aaaatctttt aacaaaacat aaactcccca aaatttccta caagccaaac      300
agcattgtca caccctcaca agctcttatt acttacacag ccaaatgact caagattact      360
aacgtttcta ttcataagga gtttgctggc ctcagatcaa cacaatcaag ccctccccca      420
ccttccttct ctctcccctg ggagactgac gtttggaact cacgccgcac caggtttttt      480
cagaatgaag acgatgtgtg ttcgctgctg gaactgtttg tcctgggatt ttataaacac      540
ctcccccact cctttttaaa gttctgtttt tgaggtgggg gaaaaggagg tcggaatctg      600
tttagccttt aaatctccca attcagaaat atattctaag aatttaatag aaaaagacca      660
agggctgtgt ctgctattta ctgcagaact gggtattcct atcagaaatc acctacatgt      720
gtcaccaaga tcagagacaa ggatgaggga acagcatga tccctgcctt ctggagggtt       780
acagttgaag cttccgctgc ttctgcactt gacctcaaaa caaacaaaaa acccaccgca      840
aacaacaaca aaaaaatcca ggcccacctt tcccccttgga tctttcactt gacagctttc     900
tcggcccaaa ataaggcacc ctacatctga atgcatccct aaggccttac cgcacccagt     960
ccaggaggca gtcctggcag ctgccctcca ccgaactccg cgcttttcca cacacgctcg    1020
tggaaggaga aaaccgctca aacaactgga ctcggcccgt ttcctttcgg taacctcccc    1080
acagcccaac acgctgtccc cagacgctgc ccgctcccac cccg                     1124
```

<210> SEQ ID NO 28
<211> LENGTH: 250
<212> TYPE: DNA
<213> ORGANISM: Homo sapiens

<400> SEQUENCE: 28

```
gggagcagga aggtatgagc ctcagctgag cgaaaccctc cttgcagcca ccacggaggg       60
acggggcgcg tctccttctg aatgacgcaa ggggcggggc gcgtggtggg gcggggaagg     120
cgcgaggcgc gccgcgatcg gggactgtcc taagacgggg ggggcgcgct gcgctaggga    180
ctgtcataaa aggggcggga cgcgccgcgg tcgggatgac gtgagctggg ggcgctcgtc    240
gctgcagccg                                                          250
```

```
<210> SEQ ID NO 29
<211> LENGTH: 56
<212> TYPE: DNA
<213> ORGANISM: Homo sapiens

<400> SEQUENCE: 29
gaccagcaga gcaatccgaa acccagccca cgtgggttcc cagaccacca actccg        56

<210> SEQ ID NO 30
<211> LENGTH: 253
<212> TYPE: DNA
<213> ORGANISM: Homo sapiens

<400> SEQUENCE: 30
gatgagcctg gcttcggcgc tgacgctctg gccctggggg ctgcctggct ggtgtcaggt     60
agcggaagac gcctggagag tcactcgctc cttcccccac ccgcccccac cgctgctcgt    120
gccaggacgc gcagtttgca gttgcagctc tggcactggc gcgggatggc ggagcttccc    180
ttggatggcg tcagggtcac tgagtgcaca gcctacctgg tctgagggtc tgctcctcct    240
ggacacctct ccg                                                      253

<210> SEQ ID NO 31
<211> LENGTH: 232
<212> TYPE: DNA
<213> ORGANISM: Homo sapiens

<400> SEQUENCE: 31
gtgcggggga acgagaccct gcgggagcat taccagtacg tggggaagtt ggcgggcagg     60
ctgaaggagg cctccgaggg cagcacgctc accaccgtgc tcttcttggt catctgcagc    120
ttcatcgtct tggagaacct gatggttttg attgccatct ggaaaaacaa taaatttcac    180
aaccgcatgt actttttcat tggcaacctg gctctctgcg acctgctggc cg           232

<210> SEQ ID NO 32
<211> LENGTH: 559
<212> TYPE: DNA
<213> ORGANISM: Homo sapiens

<400> SEQUENCE: 32
gctgcatcca ctgggtctct ggctacaggc agagagccag tcagcagtgc ccctgcagct     60
gtttggggct gggggctccg atgatgccag agccctaggg tttacaggca cctaggcaga    120
ttcgaggatc caagtccctg ccacatgcgt ttgggtgaga ccgacctcac tgcctcagtt    180
tcctcctata cactgatgct atcaacaaaa atacccactt caggaggtgg ttgtaaagat    240
tatacaagag actgcagagc gttaggcagc acctggcaca agacaaatgc tcagtaaaag    300
accactgctg tcattaaggt caacaccagc cctgagctcc tgccctggag ctgacccagc    360
gctcacgccc aggatcagaa agggagggct ggggctgatg agctgggagg tggtgtgcgc    420
ccttctcctg cctccagctc ctctctggac ccctgtcctg gcacctcttc ggtccctggt    480
tcggtctgcc ccttttcccac cgcggcccgt cttaggccag gatgtgctcc ctgccctgcg    540
gactctggag cagggcccg                                                559

<210> SEQ ID NO 33
<211> LENGTH: 389
<212> TYPE: DNA
<213> ORGANISM: Homo sapiens

<400> SEQUENCE: 33
```

```
gggcaacct agaatccacc agtggggaga gtaaggcgac tcggagaaag gcgaggggct    60
aatgcatccg ttctaataac tctgacttta actcggggct agatgggaa acactggaca   120 gttctaccc gaggtgtgac agaacttgac cttcatttta aatcggtcca tctgtttagg   180
ctagtgagaa aaacaatat ttgaactcgg gcagtccagc tcaggagtct gtgctgtcgg   240
gattaaagaa tcagtcgaca cccccagggc tgagccccgc agcaagcgcc ccgcgggtgc   300
tggcccccag actgtggtta ccgccatcct ttcacttaaa ctccgccccg attactcccc   360
cgctccaggg ctccgcatcc actctgccg                                     389

<210> SEQ ID NO 34
<211> LENGTH: 45
<212> TYPE: DNA
<213> ORGANISM: Homo sapiens

<400> SEQUENCE: 34
ggctgggggt ggggaaggga ggccgccaca gctcccgccc cgccg                    45

<210> SEQ ID NO 35
<211> LENGTH: 67
<212> TYPE: DNA
<213> ORGANISM: Homo sapiens

<400> SEQUENCE: 35
ggggattcgc gctgggctcc gagagcccgc agaaccagcg tcgtgtcctg ggcgagctgg    60
gaggccg                                                              67

<210> SEQ ID NO 36
<211> LENGTH: 3776
<212> TYPE: DNA
<213> ORGANISM: Homo sapiens

<400> SEQUENCE: 36
ggagttacac tcgaagtaga gaaacggaaa ccccattata ttagctacct tttcggcagt    60
gcaccaaccc tctaccgcct gccatacagc cttgaagaaa gggcaggtca ccttccccca   120
cctgtcccca cctctccttt cctccttgtc tttaccaca gcttcaccaa ggccctgaga   180
tgcttccgcg gtgtggttaa aacctggctc tattctctga ctgtccttcc ccaggagtgg   240
ttctctccca gctgctctcc cctcccaggg tctccttcct actcccactg gccaaggcag   300
ggcatacccc caatacaccc ctcaccccac atctcagaaa tactccttta tctattttct   360
cattcaagag agctagaatt ttaaacagta aattccttgt gaaatgctgc aattactcct   420
tttaaatgaa agatctagaa gaaattggaa tctcctttct acagtgaggg atgcagacaa   480
aagaaaacaa ggaacttaag ggaggattgg ccagatggaa gtcgggggaa ctttgctggg   540
atctgtagag ggcagaacca gcctggctgc ctcaccaccc tcgccatccc tcccgagtgt   600
gtggcacatc actgtatcct agcgtttgcc atgttggact gtcctggttt actgccgtgt   660
atcttccaca ttggaccacg agctgcttga gggtagggtc atatcacctt tgtcttttta   720
ttcccagtat ttcaaatgtg gctgacacac agagagctct gaatacagac acacgcagag   780
caaaatgcct aacacgattg agcattcgta ccaggccctg ttctaagagc tttagaccca   840
ataagtcatt tacttcccac accaacctta caagttaata ctacattaat attccaactt   900
cataaatgtg taactgaagc acagaggggt ttaggaactt gcaccaagtc acagagcttg   960
aaggatccat ggcttgaacc caggcaggct gactccaatc ttagctttaa tgaatgaatg  1020
aataaaagaa caaacaatac aacaaatgag tgtgtcttgc ttttggccaa ggggtttatt  1080
```

```
taaaattatc atttcagaaa tctttctgcc cagtgatctg actttgtttc aaattgggac    1140 ttttttttt tcttagcta acccaccttaa aatcataag tcagttttcc tctctcaact    1200
tactggagac atttctgatt aatcaagtac gttcatgcat ttcctcagaa tggtgaactc    1260
atcattagtc cgtccctatt taactttttc cacctgccct cagctgggcc aaccccgagc    1320
tcctcaacca cagtcagtcc tttctccttc cctccctccc tccctcccct tcctccttcc    1380
ctccccttcc tccctccctc cccttcttcc ttctctccct tctctccccc atccctccct    1440
cccttcctcc cttcttcagc cacatcttgc tccaccccc tatacatacc tgcggcatca    1500
gccttaaggg atcctttgcc actttctctt cagagctgca ttttaacatg tgcaacatta    1560
tttggatggt ccccttagca tgtgtggccc acttgctatt tgcttttcat ccagacctag    1620
ctcaagtatc cctttctctc tctgtctctc tgtctgtctc tctctctgtc tctctctgaa    1680
gcttcctcta gccccaacag atgaagtgct ccctctgggt gctctgggag catcgtgttc    1740
ctacttctgc tgtagtgctt atctcagatg gaattgaatt ttacggttag tgtgtgtccc    1800
tcccaattaa actttaaact ccttgaagga aggcatattt cttgctccta tctgtctctg    1860
ctgacatggc aaagagacct ggcacaaagt aaagacacaa tagatacttg ttttattgca    1920
tttgcctgtg aacatatgat ggattgaaca cagttttacc agttcacctt aaaaatgact    1980
acttaaggct gcttatgcat ggcacaaaga cacaacatgc atcaaatcct agcagagagt    2040
acattttcct ggtccttcaa gtataagaaa accttgctat ttttgcctgc gtatggtttt    2100
aataggattg ataaaacaga agagagatgg ttccctaaat cagtttgagg tattcaattc    2160
agtttagcag ctcaaaaggc tgacatttgc cttatttgaa ggttggacag ctctgcagct    2220
atttatctgc tttattgcaa tgggagtgat gactgcatag gcaagctgag aagctggcat    2280
tggggaaatt gccagaaaac ttcatatagt gtaaaatatc atatagtgta aaatgatcag    2340
aaaagtgata tacaaatgct gcatgaacaa ataattatgt aaactatgta agtcagagaa    2400
actaaaatct taaagtcaga ggcttttttgg ataattaaat tgttttaacc cacccacaaa    2460
cctactgcag gaatgattct attccaaaga aatggttaat agtaagacca gaaggggaaa    2520
aaagaacacc agggagaact aaagtcaatc caaatccaag cacaagctgc tgttgacatg    2580
ttacacataa aaaggcttgc tctggggctt gcaggtcctt cttagcagag cggtgagaaa    2640
acttaatgtc cactgtgggt ggcacattgt ggtgtcactg gcagttgagc tgtttggtat    2700
cattgccatg gcattactat gcattcctct gcaaactgca tctcgctggc ttttctccaa    2760
gccaaataaa acacaaaatg ggtcaggctt agtgagactg aaatgttgcc tccttttccct    2820 ctgccttgtc ctcagctagc tttaaggcaa gcatcacatt ggattcaaag accagctgat    2880
gctctttcag tatgattact tatgctgtga ttgacaatgt ggaggaaata gcgtatatgg    2940
ccaacgatag ggcattgact aagtaggtca ttattcagcc aaacaaaggt acagtatgct    3000
gtgattttaa aatgatgccg tagattacta aattacatga aaatatactt gtaagaatat    3060
tatgtgacaa agaagcatgc tataaaagtg tagtcactgt tgaatcctat tgtataaaat    3120
gtgtgtaagt gtatacacaa aaaaactctg aaagagtaca cactttagtg ctaagagtac    3180
ttatctctgc agatctttat ttttgtcttt tttggaaatc tcgcttgctt ttatgataaa    3240
tttgcaaggt tactcttta agtgttactt tatcattaca ggaaagaata gagagaataa    3300
attctcttcc cctgggaata aatttaagag ttttcaaaga gaattacagc ctatgtaata    3360
tccagcgata tttggactcg aatagaaagt tctgaatcaa agagttgcgt agaatatcaa    3420
gggatgatct aacagccatc ctcttgcctg ggatacccac agccccattt actcaggctg    3480
```

-continued

```
tgggctcact gagaaggaga caacattggc cactgtttta ctttcttctc tgttaaagct    3540
gccttggtcc ttctgtctcc tctgatagta tcgagtcatt cagatgtatt tgctttagtt    3600
gattgccatg ctttcaaaca ggttccataa gctacacatc cacttttaag actaaattga    3660
gcttcattga atgtccttaa tgaccacaac taattcctag cccaaaggag ggaagctgca    3720
gccaactccc tcaatcctca agaacaacaa tgccgataga acccctgtgt gatccg        3776
```

<210> SEQ ID NO 37
<211> LENGTH: 237
<212> TYPE: DNA
<213> ORGANISM: Homo sapiens

<400> SEQUENCE: 37

```
gagtgaggcg gcgcaggccg cgcgggaggg cctctgcctg ctgcagcgca gggcgggcgg      60
gggcgggggg gcgcttaccg tgagcggagc ggatcggcct gactggagcc ctgaggagga     120
ggagaaagag gaggaggaaa aggaggagca cgaaaaacta cactgcggcg acggcggcgg     180
ctcccattgc ggagctggca gccgagccgt ggaaagggggg gggctctcgt gcagccg        237
```

<210> SEQ ID NO 38
<211> LENGTH: 100
<212> TYPE: DNA
<213> ORGANISM: Homo sapiens

<400> SEQUENCE: 38

```
ggcctagctt tggggcgcag gcgcgctggc cgccgcggcg ggggtcggc cgccagtgac       60 gtcaggacgc cgtgcgggtt ccgtccccca acaagccccg                          100
```

<210> SEQ ID NO 39
<211> LENGTH: 334
<212> TYPE: DNA
<213> ORGANISM: Homo sapiens

<400> SEQUENCE: 39

```
gggcgggtag gggtgggtca tgttccttgg cttgggggca gttacaaggg tacagtgggg      60
cttgttgaag ggcaaaagtt ctgtaagttc gtcccgacag gccaaagaaa ccccagagcc     120
gtctttcgac tgactacagc ctggaagaga ggccaagacc actccctgcc tctattgctc     180
catttctgag ttggtctcac tttccacccc actgacggcg cgctgcgtga ggggcggggc     240
atagagggag gggagggggct atgcgaaaga aggcggggag agtgggggtgg ggccgctcct   300 tggaacggaa gcgcgcggcc tcgaggccct tccg                                 334
```

<210> SEQ ID NO 40
<211> LENGTH: 33
<212> TYPE: DNA
<213> ORGANISM: Homo sapiens

<400> SEQUENCE: 40

```
gtgtcctaaa agatgagggg cggggcgcgg ccg                                  33
```

<210> SEQ ID NO 41
<211> LENGTH: 254
<212> TYPE: DNA
<213> ORGANISM: Homo sapiens

<400> SEQUENCE: 41

```
gatgccatct gcggctgctg aaggaggcgc ctccagaaaa gatgccgagt gttgcaagct      60
gtcgatgcag ccaagagccg aagaggcatc ttgccgattg ggagggagc ggcgcttacg     120
```

```
tgtttattgg cttaactctc ccgtgtccgc ggcgtaaagg gctgctgcag agggctggag    180
gggggagagc gcggagcgtc ctcagagcct cagtacttct gaccccaata ccttgccacc    240
ctcctcccct gccg                                                     254
```

<210> SEQ ID NO 42
<211> LENGTH: 46
<212> TYPE: DNA
<213> ORGANISM: Homo sapiens

<400> SEQUENCE: 42

```
gggggcgagg ccgttccccg cccgttccca gggcccgccc aggccg                   46
```

<210> SEQ ID NO 43
<211> LENGTH: 286
<212> TYPE: DNA
<213> ORGANISM: Homo sapiens

<400> SEQUENCE: 43

```
gaggcaggag gatggggagg aggcggccag gtctgcggca caaattaggc cattaattcc    60
tgcctgctcc tagagaaggc aaagtttctg tcctggaata cgtttccaaa gacacagctt   120
ctggaagggg aagggaaagg atggagaggc tgcgcggtgc tgatttcacc cgacaggcaa   180
tgctcgcgtt ccttggagtg ggaggggtcg ggccgatgag aaacctctgg gggatcgggg   240
caggtggaca cgcgcgctcg gagctgtcca aggcctggtc tccccg                 286
```

<210> SEQ ID NO 44
<211> LENGTH: 57
<212> TYPE: DNA
<213> ORGANISM: Homo sapiens

<400> SEQUENCE: 44

```
ggggcgagcg gctgtgcgcg gggccaaggg cggggcagc aggtgagtgc gcggccg        57
```

<210> SEQ ID NO 45
<211> LENGTH: 964
<212> TYPE: DNA
<213> ORGANISM: Homo sapiens

<400> SEQUENCE: 45

```
gcccactgat ggagttataa aggtgaagaa ctagtctagt gaagaatgca gactgagagt    60
aaacagacaa atacaatgtg actgagctgt attgttaaat acaagaaagg actatcagga   120 agacttttg gaaaaagaag catctacact gagaccataa aaattagtag gagtcagtca   180
aataaatgtg ggaggaggag aaagggatta ttccaggtaa agaaaacaag ttcaaggctt   240
gagaggtaaa aggtggcttg gtgtggtgga aaaggtgaaa gaaatttgcg actgagagc   300 aagaaatatg gtcgagaagg actaaaaaaa agtagacagg gagagcccag atgctgaagg   360
gtctagaaaa cctcagtatg gttttggagc tttgccctga aagcaataga atgcctttga   420
attgtctgaa gcagatggta acttgatcag gtctgctttt tgcaaagtgg agaatgcttt   480
ggaaggaagc aagtgtgcac gcagcgggac ccattagact aatgtataaa tcctgcctgg   540
aggtcatcac tggacagggg aggtgggga ggcggtgaag ataaacaaaa ggggataaat   600
ttgaaatatc ctgttttaaa aggaggtaga atccacagaa cttggcaatg gattggatgt   660
gagaagtgag aggaatcagt gatgactgcc agctttctga cctgaacgag tggatgaagg   720
gaagccgagt tttggggga aagagaaaca tataatacca acatttaaaa cataataaga   780
ctaagaggct gaaggaaagg gtagaacctt caatctgagc cgagcgggc cgacagcgct   840
```

```
gggcagcatc ccacgccttt ttctccgcga ggcccacgca accagccaac taaagcgaag    900
aaccacgtga gggagacccc actgcgcacc aggcgcgagc cctgcgcatg cccgttgggt    960
cccg                                                                 964
```

<210> SEQ ID NO 46
<211> LENGTH: 252
<212> TYPE: DNA
<213> ORGANISM: Homo sapiens

<400> SEQUENCE: 46

```
gaggtggcgg gtgggagagg gaatgagcag ggatgcaggg taggccctga gttgctgggg     60
gctcagcatg gccgctgcgc acattgcatc attttgtcga cactggtgtg ggtgaaatct    120
tccaaaagaa attaaaacag aaaaaaaaaa aagaagggt ctgggactta gcagaaacaa    180
gccacaatct ccagattcta ctattcctgg gccacgtgag gagcgcccac ccgtctggcg    240
ctgcgttccc cg                                                        252
```

<210> SEQ ID NO 47
<211> LENGTH: 300
<212> TYPE: DNA
<213> ORGANISM: Homo sapiens

<400> SEQUENCE: 47

```
ggcggacccg agcaaatcag caagcctgct cctccacggg gatggggac ggcgggggg      60 aggaaaagga gagtgtgtct gtgtgtgtga gtgtgtgtgt atgtgtgtgc gtgcgcgcgt    120
gtgtgttgcg cgcgcgcgcg cgcgaacagg gagagagggga gaggggagaga gagaaggaa   180 cagggagagc gcagagagga aaactgcaga aaaccacagg gaaagtacgg taccgcctca    240
gatcttttca tttaaaaaaa aaaaaaact tacttctagt tcattttccc atcactcccg    300
```

<210> SEQ ID NO 48
<211> LENGTH: 118
<212> TYPE: DNA
<213> ORGANISM: Homo sapiens

<400> SEQUENCE: 48

```
ggtggggtga ggagaggagg ggctggggga gggggagaga ggcggggtga ggggagcggc     60
gaggacggga cggagggaga gggggcgaga gagatggaag gagagcgagg agccaccg     118
```

<210> SEQ ID NO 49
<211> LENGTH: 50
<212> TYPE: DNA
<213> ORGANISM: Homo sapiens

<400> SEQUENCE: 49

```
ggcgggcccc aggctgcagg ggcggtggcg gcgctgagct gggcgggccg                50
```

<210> SEQ ID NO 50
<211> LENGTH: 45
<212> TYPE: DNA
<213> ORGANISM: Homo sapiens

<400> SEQUENCE: 50

```
gactcggcgg gcatcgccct ctacagccgt gagtacgggg ccccg                     45
```

<210> SEQ ID NO 51
<211> LENGTH: 1340
<212> TYPE: DNA
<213> ORGANISM: Homo sapiens

<400> SEQUENCE: 51

```
gtagctttca aaacgacaaa ctaggcaaac tatacatctc caccactcca attttgtcag      60
aatgctaatg agcttgctct gatctttact cggcttcccg tgttttctac atcttcaagg     120
accacatggc gctagcaaaa taaagacaac taaatgagaa tttcgaatgc tttttgtgtt     180
aggacctggt gcttttcagt ggacgcactc gttgaatatt ctcaacttaa aagagtacaa     240
caggggttg ggtatgaact ttttaacagg aggaaatttg aacaaaagta aattagtgag      300
atgaggaaaa tatgagaaaa atttctgatt aatttccact ccataatatc aatgacacct     360
tcagccccac tcatactctt ctaacaagag atgctgataa agatgaatg attctgtgtt      420
gttcacagtg aatgtttagt ggttttttaa tagcagcatt ctacataaaa ggcaccagga     480
agtactccgc attagcagtt gagatcacta gttaatagga tgatgtcttt tagcttttgt     540
cacaagatta ttagaaagga tgggtttctg ttctcatcat tgcatagttt ggagtgcctg     600
ttgagtacaa gtgctaaaat acaggtttct cagtattgtt tcacatgtaa agcaaaaagc     660
cttttaatgc aacacctttt cctttttac caggtgattt tgttattgat ctctaatctg      720
cccctttagc tgtattaaat gcttaaagtg ttctgctttt ccatgtagcc ttgatgctag     780
ctatttgtgt ctataaattc attaacatta aaacaggatc tatatagact attagagtct     840
atgagttaga aaatggcata ttacatactt gtttagggca taaataacaa cataaattta     900
agattatctg cataaatgtt ataaaaatat gttcgttgat aatatgttat gagatttaa      960
ttatgtattt ataaggaaca tattttcac aatctctctt ttctttagca atcactgtac     1020
acttaccagg agaataagag tagtcaactc catttcttac catatccatc catacctaga    1080
aagaagaaaa aaccaaaact gggtacattt ttatatataa agatatttga acacggctgg    1140
gcacaggctc acgcctgtaa tcccagtact ttgggaggcc gaagcaggtg gatcacctga    1200
ggtcgggagt tcaagaccag cctgaccaac atggagaaac ccgtctcta ctaaagatac     1260
aaaaattagc cgagtgtggt ggcgcatgcc tgtaatccca gctactcggg aggctgaggc    1320
aggagaatcg cttgagcccg                                                1340
```

<210> SEQ ID NO 52
<211> LENGTH: 282
<212> TYPE: DNA
<213> ORGANISM: Homo sapiens

<400> SEQUENCE: 52

```
gagcttgcca agagtctatt ccagcctaca ccgctaggaa gccaacttca gcagctcaa      60
tgagggggacc aaactggggc tcgctttcca aacgctccgc tccaaaatct gactctctct   120
ccagccccga tctcagtgtg agccgaacct cagaaaagac gcttttttaag ggcgacacag   180
ggttggcttt acagcggggc caagaagact acctgggggt accgccacct cggacaaatc    240
cgttggctct gtccaaggtg ctgaatggac tcctatcgcc cg                       282
```

<210> SEQ ID NO 53
<211> LENGTH: 46
<212> TYPE: DNA
<213> ORGANISM: Homo sapiens

<400> SEQUENCE: 53

```
gcgccctcct tcccgcccag gccttccgcg ggcacctcag gccccg                    46
```

<210> SEQ ID NO 54
<211> LENGTH: 720
<212> TYPE: DNA

<213> ORGANISM: Homo sapiens

<400> SEQUENCE: 54

```
ggctccagtt tctttatgcc tgattgcctg ctactcgagt cgtgcccatt ttcctctctc    60
ctggcccaaa cttcctgcgc ctacagccgc cttcaggcac ttgtgtgagt ctctgtttaa   120
gagatcagcc aggaggtgga acctcacagg acttctgtgg tcaagaaact gtgtgagcgt   180
gttctcacac ataggaagaa agcaatgtat gtcatagatc cccaaaagga tgaatgcagg   240
aagagggaag gaacaaagga aggaaagaaa ggcagaaagg aggaagaaaa aaaaagtaat   300
taaaaagaat gacgtgagga ttgtttgagc ccaggagttg gagatcagcc tgggcagcac   360
tagggagaac tcgtccctac aaaaaattta aaaaattagc tgggtgtggt ggtgcgcacc   420
tgtagtccca gctactcggg aggctgaggc gggaggatgg gaggatcgc ttgagcccag    480
gagttggaag ctgcagtgag ctatgattgc accactgcac tccagtcggg gagaaagaat   540
gagaccctgt cacaaacaaa caaaaaagca aaagaatga cggaaggtta ggaaagaagc     600
agagcaacga agcagaggcg cccagcggcg gactggccag ggactgagcg ccgtgcacca   660
cagagccctc ctcgcccact tcccgcggcg agggtggcgt tgctcccact acccgaccg    720
```

<210> SEQ ID NO 55
<211> LENGTH: 231
<212> TYPE: DNA
<213> ORGANISM: Homo sapiens

<400> SEQUENCE: 55

```
ggaggcggtg gccgagagcc tgctcctgga gctggaggag gtgacccccg ccgaagacgg    60
cgtctatgcc tgcctggccg agaatgccta tggccaggac aaccgcaccg tggggctcag   120
tgtcatgtgt gagtggccca ctctgtgcgt ccacacgccc acctgcagcc gagagataaa   180
gggaaagggg cctcatccag ggcgagcatg ggctgggtcc gaggggacc g              231
```

<210> SEQ ID NO 56
<211> LENGTH: 84
<212> TYPE: DNA
<213> ORGANISM: Homo sapiens

<400> SEQUENCE: 56

```
gccccgctga gccagcgcaa ctgtctgagg tggaagccca cacggaccac agctccagga    60
agccgagcaa gaaacgaatc gccg                                           84
```

<210> SEQ ID NO 57
<211> LENGTH: 466
<212> TYPE: DNA
<213> ORGANISM: Homo sapiens

<400> SEQUENCE: 57

```
ggtggcgtcc aaaacacaca gggaccttct ggaggtaaat ctgcagaatg gcattttgtt    60
tgtgaattct cggatcgatc gcgaggagct gtgccagtgg agcgcggagt gcagcatcca   120
cctggagttg atcgccgaca ggccgctgca ggttttccat gtggaggtga aggtgaaaga   180
cattaacgat aatccacccg tcttcagggg cagagaacaa ataatattta ttcctgaatc   240
tagactcctg aattcgcgtt ttccgataga aggagctgct gatgcagaca ttggtgctaa   300
cgctcttcta acgtacacgc tcagcccgag tgattatttc tctttggatg tagaggcaag   360
tgatgaactg agtaaatctc tttggcttga attgagaaaa tatttggata gagaagaaac   420
accagaactt cacttattac tgactgccac tgatggggc aaaccg                   466
```

<210> SEQ ID NO 58
<211> LENGTH: 331
<212> TYPE: DNA
<213> ORGANISM: Homo sapiens

<400> SEQUENCE: 58
gaagccaggg ctcccagcgt ctagtcaggg gcgcagaaac cctcgttcct ccaaaccccc      60
gccacaggga ccactccaga agaaacccat tcgtgatttg gtcccttttg tgtttgagta     120
ttgtggggag tgggctatct agactctaag gactccaagc taacgatgac ctgtgtgggc    180
cttgctctga acagaaaact caaactcagc gtgggttccc cgtcttccc caaaaggcca     240 aggcccaaag aacccttttc atttggcgag gggcttgagg aagggagggg ctggggcggg    300
agagggtcgg ggtctgcaag ccagcggccc g                                    331

<210> SEQ ID NO 59
<211> LENGTH: 282
<212> TYPE: DNA
<213> ORGANISM: Homo sapiens

<400> SEQUENCE: 59
ggtggtgagc gagggcggca agcccaaggt gcgcgtatgc taccgcgggg aggacaagac      60
gttctacccc gaggagatct cgtccatggt gctgagcaag atgaaggaga cggccgaggc     120
gtacctgggc cagcccgtga agcacgcagt gatcaccgtg cccgcctatt tcaatgactc    180
gcagcgccag gccaccaagg acgcggggc catcgcgggg ctcaacgtgt tgcggatcat     240
caatgagccc acggcagctg ccatcgccta tgggctggac cg                        282

<210> SEQ ID NO 60
<211> LENGTH: 99
<212> TYPE: DNA
<213> ORGANISM: Homo sapiens

<400> SEQUENCE: 60
ggttcccgca gccaccccga agaccccag gcagccgccc agcaccagca gtagcagcgc       60
tgggctgcag gagggcaggt ggcgggggct gccccgccg                             99

<210> SEQ ID NO 61
<211> LENGTH: 229
<212> TYPE: DNA
<213> ORGANISM: Homo sapiens

<400> SEQUENCE: 61
gggccactga cctcgaagct tatgatggtc gtggtgtgtt ttttgcccgc ggcccagacc       60
gcttcctggg ctctctccag ccgccctcct ggtctcccct gggaccgttc cgaggtgtgg     120
ttccctggcg cccgccgttg ctcccgtagt ttgggttctg tcgctcccag caggtctcgc    180
ttatgccgcc cacccgtgc cctgctcttg cttgctctgc caccccccg                  229

<210> SEQ ID NO 62
<211> LENGTH: 59
<212> TYPE: DNA
<213> ORGANISM: Homo sapiens

<400> SEQUENCE: 62
gagggcgcgc ggcgatggcg gcggcgggca ggcggcgggc gcggcgggcg aggggtccg        59

<210> SEQ ID NO 63
<211> LENGTH: 275
<212> TYPE: DNA

<213> ORGANISM: Homo sapiens

<400> SEQUENCE: 63

| | | | | | |
|---|---|---|---|---|---|
| gcctatcctc | cctgcaggaa | gtgcgagcgc | accacgtgcc | atgacttcct | ggagtgccag | 60 |
| aactcgccag | cgcgcatcac | gcactaccag | ctcaacttcc | agacgggcct | cctggtgcct | 120 |
| gcgcatatct | tccgcattgg | ccccgcgcca | gccttcacgg | gggacaccat | cgccctgaac | 180 |
| atcatcaagg | gcaatgagga | gggctacttt | ggcacgcgca | ggctcaatgc | ctacacgggt | 240 |
| gtggtctacc | tgcagcgggc | cgtgctggag | ccccg | | | 275 |

<210> SEQ ID NO 64
<211> LENGTH: 305
<212> TYPE: DNA
<213> ORGANISM: Homo sapiens

<400> SEQUENCE: 64

| | | | | | |
|---|---|---|---|---|---|
| gtgcccgact | cagggagtga | tgtcgagaca | cacacatcac | caggaagagc | ccaggggtgc | 60 |
| acagtgcccc | tcaaggcact | aaccgtagag | gcgtgagtag | catagggctt | gtgcacaccc | 120 |
| aggcatcggg | tgtcgagctc | aaggcgaggg | agtgtgccag | cggcacaggt | cagggaagtt | 180 |
| tgtgaaggag | accaggtggg | agccactcac | agaaatcagt | aacatgaaaa | ccacagccac | 240 |
| aaaaccacca | ctgtcactca | acgcccatca | tcacgggcag | acagttcta | catcatctcc | 300 |
| ctccg | | | | | | 305 |

<210> SEQ ID NO 65
<211> LENGTH: 1173
<212> TYPE: DNA
<213> ORGANISM: Homo sapiens

<400> SEQUENCE: 65

| | | | | | |
|---|---|---|---|---|---|
| ggtggctcag | cccagctcct | gcctaggaaa | gccttagtgt | tgggagggac | cctgatgact | 60 |
| gaggagcctg | gtagctccag | gtcgcccaca | ctttcaggtc | tcttgcacca | gaaggtggca | 120 |
| ggatccattg | ggaggaaaca | ggccaccttg | gaaggtgtcc | ctgggccccc | atccccaggg | 180 |
| attgaggccg | tagggggccc | gctctgctgc | gttgaccaga | ctcctgggct | ttgaaggctc | 240 |
| ctgggcccag | taagaaggag | gtgggtgcca | aggttgagga | ggaagcatcc | gagtatgtgt | 300 |
| aggaggagga | cagggtgtga | ccatagactg | ccaaaagctg | caggtggatc | gggggaccct | 360 |
| gggggctcag | gatccagcaa | ggggcggcag | gagtaaagga | ggaaggaatg | acaggtgcaa | 420 |
| ataccttccc | accaaagccc | tttatgccct | ctggctcctc | cccagagttg | tccccactct | 480 |
| cagtcggtca | cccactcctt | gaacttgaga | tcggtgtcgg | tggtgctaaa | gccatcatca | 540 |
| gcaatgacat | catcaccccc | tcctcctcat | ggatgaccgt | gtgctcctcg | tcactcgcta | 600 |
| tgacctcgct | ggccatgtgc | tgggaatgag | cagctcacgt | gggcggcagc | agggctgccc | 660 |
| acgggtcacc | tccctcacca | ggggctgcaa | agtggcctgg | agctccatgc | tgagtagaag | 720 |
| gctttgggcc | agagtatgat | gcagtgccag | acaccacctg | tgtcagttcc | cgtagtgcct | 780 |
| gacggtctat | ttccctgccg | tccaggctgt | gtacccgct | gtgggagaag | gcttgggcca | 840 |
| ggctgagcca | ggttccctga | ctgtgtgcag | ccgttctgcc | ccacagaagc | tgctccttgg | 900 |
| tatccgagct | ctggagtgtt | tgggctgcaa | ctgacaggag | ttcagaggac | accccagggg | 960 |
| cagtggcagt | gcccgtctct | gatatgctcc | gctcccacga | gccttgtta | cactcctgct | 1020 |
| agccctggc | ttgtgggctt | ggcctctgag | ctggacttct | ttcggtcctt | gttgcaagtg | 1080 |
| ggccaccttc | acctggaagg | ccaggtcgta | tttctgcatc | tcattgggcc | ccagggtgta | 1140 |

```
ccaccgctcg ctcagcatct ggctgacggt ccg                           1173
```

<210> SEQ ID NO 66
<211> LENGTH: 400
<212> TYPE: DNA
<213> ORGANISM: Homo sapiens

<400> SEQUENCE: 66

```
gaaaacaaaa ggctgaagac agaaaaagaa gacatttact attccacttc ttccttttac    60
atcagtgaga gaaagggcct tgggagaaag atggcacaga gagaaacaaa agaaagaaag   120
aaagaaaacc aaaaatctct gctttctcaa aaatccctgg tctgcctatc taggctggga   180
gagaccccga gggcagcctg tctctcctgc agcctttgca gtcagcgaca ggcatcatga   240
aattaatttg aaataaacaa tgacaaagca ggaagctcaa cgggtccctg agttgctttg   300
ggccccccact cctccccgaa gcccctgggc tgtttaacaa agccgtgggt ccgcctaccc   360
caagcacttt ttgtgacgtc acagctccga ggaccatccg                         400
```

<210> SEQ ID NO 67
<211> LENGTH: 256
<212> TYPE: DNA
<213> ORGANISM: Homo sapiens

<400> SEQUENCE: 67

```
ggggccgaga gggcgggagg gcgtagtggc ggcccgtcgg ggcggctgag gcgggcagcc    60
gaagcagtgg ctctcggagg gggaacaaag agcagcgact aaggcggcag aggagcggcg   120
gcggtggcgg cgctgcagca gcgggcggga ctggtatggt ggttccacag ggcagacccc   180
gctgcactca cagggaggag gaggcggcag cggcggagga aggcggcgca ccccgagagg   240
tgagcgaggc aggccg                                                   256
```

<210> SEQ ID NO 68
<211> LENGTH: 477
<212> TYPE: DNA
<213> ORGANISM: Homo sapiens

<400> SEQUENCE: 68

```
gaaccaatct cagcctccct tccactagtc attagtctcc cccgctgcag gtagagtgac    60
aggcaggctc aggagctcct gaaaaggcct ttgttttatc gccttcagtt cagatgcttc   120
agagcactag caggccatat tttaatctca ggtctttgca aacaaaatcg ttaaaagcag   180
atggctgtga agactgccat gaatattaat agatattgaa aaaaaggccc cttaatcttt   240
ccataaatct ttctgaggag gtgggggaag acttggagat gagggctgca gtgtagttgc   300
aggtaccctg gcccttccta tctgggcttg atcctaataa ctgaggaatt agcacaaaga   360
taggtggttc cagcccagag ttgggcactg agatgggcct ggagaagcag tcttgggctt   420
gccatctcct gtcttccttt ctccttcccc tgcagagctg gctgggtga ggacccg       477
```

<210> SEQ ID NO 69
<211> LENGTH: 193
<212> TYPE: DNA
<213> ORGANISM: Homo sapiens

<400> SEQUENCE: 69

```
ggccctgggg cagcacagct tcccgattcc cacgtgcctc tgcgtctcgg cgccacgggt    60
gactttcggt ccagatgcca gcaaagacat ctctctgtct accaggcaac cacctccatc   120
ctcacctcct cacgggcaga ctctaactac ctccgctctc tccacaaatg ccagtgcgag   180
```
cgcagcctcg ccg                                                        193

<210> SEQ ID NO 70
<211> LENGTH: 2008
<212> TYPE: DNA
<213> ORGANISM: Homo sapiens

<400> SEQUENCE: 70
gcccgtgata atcgtgcctg cagcagcttt tcactggcta caggattcag cccttaggct      60
gaagccacgc ttggctccga agtttccact gcacaggacc agggctacca tctgacaaac     120
tgcaaggcaa gagaaaacac gtgtcctccc tgggattggg tctgggggaa ccttcatgcc     180
tcagaggaga agaacgtcac aagtagttta ggacacaggt ggcagtgacg aagctcttgg     240
ggacatggat ggtgctggca gaactcaagg gggatagagt tggtgctggc agaggtcaca     300
gggacaaaga tggcactggc agagttcata ggggacagag gtggagttgg cagagttcat     360
gagggacaga ggtggcgctg gaagagttca cgggggacag aggtggcgct ggcagagttc     420
acgggggaca gaggtggcac tggcagagtt cacgggggac agaggtggca ctggcagagc     480
tcatgggggg cagaggtggc gttggcagag cccatggggg acagaggtgg cgctggcaga     540
ggtcatgggg gacagaggtg gcgctggcag aggtcatggg ggacagaggt ggcgctggca     600
gaggtcatgg gggacagagg tggcgctggc agagctcata ggggacagag gtggcgctgg     660
cagagctcat gggggtcaga ggtggcgttg gcagaggtca cggggggcag aggtggcact     720
ggcagaggtc acgggggaca gaggtggcac tggcagaggt cacggggggac agaggtggca     780
ctggcagagg tcacggggga cagaggtggc gctggcagag cccatggggg acagaggtga     840
tgttggcaga gttcatgggg gacaggtggc gttggcagag cccacggggg acagaggtgg     900
cgctggcaga gctcacgggg gacagaggtg gcgctggcag agctcacggg ggacagaggt     960
ggcgctggca gagctcacgg gggacagagg tggcgctggc agagctcacg gggacagag    1020
gtggcgctgg cagagctcac gggggacaga ggtggcgctg gcagagttca cggggggacag    1080
aggtggcgct ggcagagttc acggggggaca gaggtggcgc tggcagagtt catgggggac    1140
agaggtggcg gtgcagagt taatgggggga cagaggtggt gttggcagaa ctcatggggg    1200
acagaggtgg cactggcaga gttcataggg gacagaggtg gcgttggcag aactcggggg    1260
acagaggtgt cattggcaga ggtcataggg gacagaggtg gcgttggcag agttcacggg    1320
ggacagaggt ggcattggca gaactcatga gggacagagg tggcgctggc agagttcatg    1380
agggacagag gtggcgctgg cagcgttcac ggggggacaga ggtggcgttg gcagcgttca    1440
cggggggacag aggtggcgtt ggcagcattc acggggggaca gaggtggcat tggcagaact    1500
catgagggac agaggtggcg ctggcagaac tcatgaggga cagaggtggt gttagtagag    1560
ctcatgaggg acagaggtgg cgttggcagc gttcatgggg gacagaggtg gcgttggcag    1620
cattcatggg gggcagaggt ggcggtggcc gagttcatga gggacagagg tggcgttgac    1680
agagctcctg ggggacagag gtggcactgg caaagcacat gaggacaaag gtggtgctgg    1740
tagatttcac tgaggacaaa ggtggcacta gcagagctca caggtacaga ggtggtattg    1800
acagctccca aggacagagg tggtgctggc agcgctcaca agggacacat gtggtgctgg    1860
caggtttcat tgaagacaaa gatggcattg gcagggctca caggacagag gtggcgttga    1920
tggagctcct gagggcagag gaggtgctgg cagagctcat gggggatgga gggtgctggc    1980
agagctcacg ggagacagtt gtgacccg                                        2008

<210> SEQ ID NO 71

<211> LENGTH: 160
<212> TYPE: DNA
<213> ORGANISM: Homo sapiens

<400> SEQUENCE: 71

| | | | | | |
|---|---|---|---|---|---|
| gactctcctt | ccatctcgcg | tcctcagcgt | ccgttgggct | ccactttaaa | aataaaaaaa | 60 |
| tcaaactaac | taaaacgaag | gtgggacccc | ccaggctccc | cttcttccct | ggcctctgga | 120 |
| aaatccagct | gggaggacgc | aggggcgggg | gcagatcccg | | | 160 |

<210> SEQ ID NO 72
<211> LENGTH: 64
<212> TYPE: DNA
<213> ORGANISM: Homo sapiens

<400> SEQUENCE: 72

| | | | | | |
|---|---|---|---|---|---|
| gtgcgcgcgc | agcccgcgag | gcggggccgt | gtcagtgagg | cctactccca | gcttttcct | 60 |
| cccg | | | | | | 64 |

<210> SEQ ID NO 73
<211> LENGTH: 2061
<212> TYPE: DNA
<213> ORGANISM: Homo sapiens

<400> SEQUENCE: 73

| | | | | | |
|---|---|---|---|---|---|
| ggccagaggc | tgtggagact | cggatcctga | ggcaaaagga | agccgagtca | gggacgcgct | 60 |
| tccttcccca | gggctcgtcc | ccagcgccac | ccgcccttct | ctagagcccc | atccccagcg | 120 |
| cgaacctcca | ggaggaagca | gcagtcacca | cgcggggaca | gaaggggggag | agctcgagcc | 180 |
| agggcccagc | gattggagtc | cgcggaacgc | agggacatga | agtccagcag | agaaaactaa | 240 |
| aaactggcaa | cacttccatg | gataaaaatt | cagcctctcc | ctctacaata | gcaacaaacc | 300 |
| ccaaaccagg | aaacagagac | ccctgtaaat | aacccaccaa | gataaattcc | acaccctcca | 360 |
| ccagtgtttc | aggctacagg | gtgggatatg | cggggaggtg | gcggagaccc | atcttgaatc | 420 |
| agaaattcaa | ggactaagtg | caaaactgga | ccctaatggg | gtgggtctag | agcattgaag | 480 |
| aaagtgcatt | agtgcttggc | tagggctggc | aggtggctgt | tagatgaggt | gcgcccctgg | 540 |
| gtgcaggaag | tgtttttttgg | gggatgacaa | cttcctaaca | ttagatggta | gtggtgactg | 600 |
| gtgattgtac | agcccctataa | atttgctaaa | aaaaaattga | attgcacatt | ttaataggtg | 660 |
| aattgtatgg | catgtgaatt | atacctcaat | aaagcttttta | tataaaattg | gatcgattta | 720 |
| actaaaaaaa | gaaattttaa | gaagagacaa | aattggttgg | gtgtggtggc | tcatgccttt | 780 |
| aatctcagca | ctttggaagg | ctgaggtcgg | gggggtggat | tgcttgagcc | caggagttcg | 840 |
| agaccagcct | gggcaacatg | tcgaaaccag | tctctaccaa | aaataggaaa | aaagtagctg | 900 |
| ggcatggttg | tgtgcacctg | tagtctcagc | tactcaggag | gctgaggtac | aaggattgct | 960 |
| tgaacctggg | aggcagaggt | tgtagtgagt | gagccactgc | actccagcct | caggaacaga | 1020 |
| gtgagaccct | gtctcaaaaa | aaaaaaaaa | aaaaggaac | aaaatatatg | aaaaatgaag | 1080 |
| actaaattac | aaaatcctta | agagaaaatg | attttaatta | aaatttaat | aagggacact | 1140 |
| gaagaaagga | aaatagaaat | tatataatga | aagaagtgaa | aagggttaga | aagactaaga | 1200 |
| aaatctaacc | aacatagaat | tggagttttt | aaaacacaaa | aacaataga | catagctagt | 1260 |
| atttaaaacg | gacgcctaca | ggtgcgtccc | acggggatg | gggacacgga | cgcctgcagg | 1320 |
| tgcacccca | cggggggacg | gggacacgga | cgcctgcagg | tgcaccccac | ggggaggacg | 1380 |
| gagacatgga | tgcctgcagg | tgcacccca | cggggaggac | ggggacacgg | acgcctacag | 1440 |

-continued

| | | |
|---|---|---|
| gtgcaccccc acgggggga cggggacaca gacgcctgca ggtgcacccc cacgggggga | 1500 | |
| cggggacacg gacgcctgca ggtgcacccc cacgggggga acgggacac ggacgcctgc | 1560 | |
| aggtgcaccc ccacgggggg atggggacac ggacgcctgc aggtgcaccc cacggggagg | 1620 | |
| acggggacac ggacgcctgc aggtgcaccc ccacgggggg gacggtgaca cggacgcctg | 1680 | |
| caggtgcacc cccacgggag gacggggaca cggacgcctg caggtgcacc cccacaggag | 1740 | |
| aacgggaca tggatgcctg aacgtgcact cccacaggga ggacgggac atggacacct | 1800 | |
| gcaggtgcac acccacaggg aggacgggga catggacgcc tgcaggtgca ccccatggg | 1860 | |
| gaggacgggg acacggatgc ctgcaggtgc accccatgg ggaggacggg gacacagaca | 1920 | |
| cctgcaggtg cactcccacg ggggatgg ggacacagac gcctgcaggt gcactcccac | 1980 | |
| gggggacg gggacatgga cgcctgcagg tgcaccccca tggggggac ggggacacag | 2040 | |
| acgcctgcag gtgcaccccc g | 2061 | |

<210> SEQ ID NO 74
<211> LENGTH: 135
<212> TYPE: DNA
<213> ORGANISM: Homo sapiens

<400> SEQUENCE: 74

| | | |
|---|---|---|
| ggaacgggcg gggcggggcg gggcgcgaag ggggcggtgc cgcgagcggg gggcggtggc | 60 | |
| ggcggcggcg gtggcggccg aggaggagaa catggcggcc gcggagagcg gctgaaatgc | 120 | |
| ctgttcttca ggccg | 135 | |

<210> SEQ ID NO 75
<211> LENGTH: 267
<212> TYPE: DNA
<213> ORGANISM: Homo sapiens

<400> SEQUENCE: 75

| | | |
|---|---|---|
| gctgcaaggc ggggctggag tggaacagga ccccgctgag cagcttggag gagtctggca | 60 | |
| ggaagaagat cgccccgaag cagagcgtga tgaaggcgct gaataccagc agcagcacga | 120 | |
| acttctccgt caggcggagg gcggcggggc ccgacccctt cctgccaccg ccgccgccga | 180 | |
| gcccccgcc caggacgccg cccgcggggc tgctgaagag cggcaacagg cccccacgg | 240 | |
| gcatcgctcc cgctgtccag tggtccg | 267 | |

<210> SEQ ID NO 76
<211> LENGTH: 239
<212> TYPE: DNA
<213> ORGANISM: Homo sapiens

<400> SEQUENCE: 76

| | | |
|---|---|---|
| gctgtagcag aggctttact gcccccacgc cctccccagc tctgccctgg tcagtagcat | 60 | |
| ttgcggtaca cgatataggg accctgttcc tcgtactgct cccgcaggac ccagcaggac | 120 | |
| tggaaggcgc gcaggaggc caggatggag ccccgatcc atacggagaa attcctggtg | 180 | |
| ggctgggcag ccaccaccac gtgggtctcg gctggcagag cgcgcagcag ctctgcccg | 239 | |

<210> SEQ ID NO 77
<211> LENGTH: 706
<212> TYPE: DNA
<213> ORGANISM: Homo sapiens

<400> SEQUENCE: 77

| | | |
|---|---|---|
| ggaagagccc agagccatca gtgtgccagt ccaggactca gctcaggaag agtcaggttc | 60 | |

```
agcccgccag gaagggtttt cagtaagtta tggaaaaaga taaatcccac acgtgtgaca    120
agagttagga ctgcatacaa atgaaaaaag ccaaacttca ctttttccac ttttatctga    180
aatgtcgcta cactgaaact tccacagaga cccacgggga cgtgtggcct gtcacaccgt    240
cggctgtatt ggatcaggat tatttcttat gaaggtctgc tttgccagta cgcagcaggt    300
cccagtctct acgccgtccc gaacacctcg tagaaatacg gggcatgcac aacgttgtac    360
ctgctccaat ctaagcagca atccagccct tttggattgc ctctacccaa acctagaaca    420
aagatggcca ggaaaagacc agggacgctc tttattaagg gaagatgcac atataatgaa    480
agataatatc caaacctctg cacgccaaca cgtgcagacg caggcacaag tcctatcata    540
ttgaaggtcg caactcactg ggaagccctt tccccagagt taaagcggga gctaaaagtc    600
cgcttatgca acaacagtcc aattactcgg acaccccgag caaaactctc cagcggaagg    660
ggcagcgggg tctgggcgc caactccctc cctgcaactc cgccg                    706

<210> SEQ ID NO 78
<211> LENGTH: 59
<212> TYPE: DNA
<213> ORGANISM: Homo sapiens

<400> SEQUENCE: 78
gggtagctgc ggccaaggcg cccgcggctt cggggggcata gcgtaggggc ccgcctccg    59

<210> SEQ ID NO 79
<211> LENGTH: 327
<212> TYPE: DNA
<213> ORGANISM: Homo sapiens

<400> SEQUENCE: 79
ggctgcagct gcttgttaac cctcagagcg ccacggcgcg agggaagggc acgccaacca    60
ggagaggggg cgagggagat gcggtccgcc tgcagtcacc tctgcacctc agagatttcg    120
ggaagtttga gtgcaggaaa gcagcgctcc gaggccaggc ctggggtgct ggccgctgcg    180 ggggggcacgc cctgcgctgc tcaggggcct gtggtttcgg agagcacccc gatccagtcc    240
cccatcgcct ctctggcagg cgttgggact tggagtgagc tggcagcctg caagtgggtg    300
gataagagcc agggcagggc agggccg                                        327

<210> SEQ ID NO 80
<211> LENGTH: 107
<212> TYPE: DNA
<213> ORGANISM: Homo sapiens

<400> SEQUENCE: 80
gctgggggcg cgggagcggc gggcgcggcg ggctggaggg cgggcaccgc gaagggaggg    60
cgccccactt ccccgcaccg cccgccaggc ccgccgagca ctgaccg                  107

<210> SEQ ID NO 81
<211> LENGTH: 661
<212> TYPE: DNA
<213> ORGANISM: Homo sapiens

<400> SEQUENCE: 81
gtcctggtgg aggcgcagct gtactaccac tggcaggcct tgcagatcct agacgagctg    60
gcagcgaagc tcaagcgcag gatgcggaaa tcttcctcac atcaaatatt tgaaaacaaa    120
ctagaaactg tccaaccgca tttctactgc gcccgcccgc agatgcagtt ttctccgcac    180
gtgcgcgcct tctctccttc ccgccctcag ggtccacggc caccatggcg tatcaggggc    240
```

```
agcagtacct gtggcagcat tggcctttgc agcggcggca gcagcaccag gctctgcagc    300
ggcacccccc agcggcttaa gccatggcgc ttctcagggc attcagcagc agcgttgctg    360
taaccgacaa agacaccttc gaattaagca cattcctcga ttccagcaaa gcaccgcaac    420
atgaccgaaa tgagcttcct gagcagcgag gtattggtgg gggacttgat gtccccttc     480 gaccagtcgg gtttgggggc tgaagaaagc ctaggtctct tagataacta cctggaggtg    540
gccaagcact tcaaacctca tgggttctcc agggacaagg ctaaggcggg cttctccgaa    600
tggctggctg tggatgggtt aggcagtccc tccaataaca gcaaggagga tgccttctcc    660
g                                                                    661

<210> SEQ ID NO 82
<211> LENGTH: 253
<212> TYPE: DNA
<213> ORGANISM: Homo sapiens

<400> SEQUENCE: 82
gagaggtgtc caggaggagc agaccctcag accaggtagg ctgtgcactc ggtgaccctg     60
acgccatcca agggaagctc cgccatcccg cgccagtgcc tgagctgcaa ctgcaaactg    120
cgcgtcctgg cacgagcagc ggtgggggcg ggtgggggaa ggagcgagtg actctccagg    180
cgtcttccgc tacctgacac cagccaggca gcccccaggg ccagagcgtc agcgccgaag    240
ccaggctcat ccg                                                       253

<210> SEQ ID NO 83
<211> LENGTH: 242
<212> TYPE: DNA
<213> ORGANISM: Homo sapiens

<400> SEQUENCE: 83
gaaagaggga ggcgcggggc cgcgcttggg gcctgccgct gcacgccagc ctgggcaaag     60
agctgccacc ttctgcgggc gaagcgggtc gggacgcagg acggcagcgg ggctggaggc    120
agctacgtgg gtccacaccc ccatgccctg caaggctcct tggccctgct tctcctctgt    180
ctcggcggga gaggagcagc ctcggtttta cagaatttca gggtcgcgtc tccagcgccc    240
cg                                                                   242

<210> SEQ ID NO 84
<211> LENGTH: 81
<212> TYPE: DNA
<213> ORGANISM: Homo sapiens

<400> SEQUENCE: 84
ggtggcgtcc aagggccgcg gggaccttct ggaggtaaat ctgcagaatg gcattttgtt     60
tgtgaattct cggatcgacc g                                               81

<210> SEQ ID NO 85
<211> LENGTH: 317
<212> TYPE: DNA
<213> ORGANISM: Homo sapiens

<400> SEQUENCE: 85
gaaggacgag ggctgcaaag gtgttttctg gagggaaacg tggagtaagg aggaagcctg     60
gaattttagc atcttcccag cgcacacggc ggctttattg gtgtgccagg gatgtctcta    120
gtctgaataa aaagggatgc tttctggctc accctgtgcc aggatagagg gaagcgtgtt    180
ctgagccagg catgggccc catctgctcc ctggcagccc ccagccgcgg cgtccgcctt    240
```

```
cctggagcc cgtccccagc cgctcacctc aggtgcagct ccagctgcgt gtagaggaag    300
tgcaggaacg cccgccg                                                  317
```

<210> SEQ ID NO 86
<211> LENGTH: 290
<212> TYPE: DNA
<213> ORGANISM: Homo sapiens

<400> SEQUENCE: 86

```
ggaaacagtt caggacgctc aagaccagaa gcgggagcaa acccaaaagg agctccaagg    60
aggtgtgtgt ggggagagcc aggggacgc aggactaggc tctttcctgc gcaaggggtg    120
gggaaacccg cgaaagccag ggagtcgcgc gcactcacgc cctcccgcca ccagggcaga    180
gccaccgctg caaggagccc acgggtgcgc gctccgctcc agggcggatc tttccacacc    240
cccctcaccc tcaaaagctc aggctggagc ggtcatcagt gcggactccg              290
```

<210> SEQ ID NO 87
<211> LENGTH: 79
<212> TYPE: DNA
<213> ORGANISM: Homo sapiens

<400> SEQUENCE: 87

```
gcggctgcgg cggccgagag gtcctgcttc ccccaggggc tggccatacc cgcggccttc    60
agcttggcct tcttggccg                                                79
```

<210> SEQ ID NO 88
<211> LENGTH: 395
<212> TYPE: DNA
<213> ORGANISM: Homo sapiens

<400> SEQUENCE: 88

```
gcaaatccgc gcagcgcatc gcgcccagtc tcggagactg caaccaccgc caaggagtac    60
gcgcggcagg aaacttctgc ggcccaattt cttccccagc tttggcatct ccgaaggcac    120
gtacccgccc tcggcacaag ctctctcgtg ttccacttcg acctcgaggt ggagaaagag    180
gctggcaagg gctgtgcgcg tcgctggtgt ggggagggca gcaggctgcc cctccccgct    240
tctgcagcga gttttcccag ccaggaaaag ggagggagct gtttcaggaa tttcagtgcc    300
ttcacctagc gactgacaca gtcgtgtgt ataggaaggc gtctggctgt ttcgggactc    360
accagagagc atcgccaacc agaacggccc acccg                              395
```

<210> SEQ ID NO 89
<211> LENGTH: 357
<212> TYPE: DNA
<213> ORGANISM: Homo sapiens

<400> SEQUENCE: 89

```
ggcgggtgtg ggatcatcta cccacccctgc ggctccttcc cgctcgcagt gaaggaagga    60
cgctcagacc aacaggggct caggtattct gggtgtcagg acccttcctc ctgcacgcat    120
cttacgcagg gtggggctga gggcgtgagg gcacaagtca ttgaggacat ggagggaacc    180
cacgctcgtc ccgatagatt gtcacggtcc tgaggcggga cggtcaggac agggaagatg    240
tatttcttcc ccctgcatcc cctcccgcac cgcgtctgaa ctcctctggg agcgcaagaa    300
cagtaacaat gctgcgcccc ttcccccacc ctttgactcc gctcgcaacc tagcccg      357
```

<210> SEQ ID NO 90
<211> LENGTH: 72
<212> TYPE: DNA

```
<213> ORGANISM: Homo sapiens

<400> SEQUENCE: 90
gtttcccgaa cctgggcggc cgtcgggcag ccccctcgtc cgaccatggc gactgacagt    60
gagtgcgctc cg                                                        72

<210> SEQ ID NO 91
<211> LENGTH: 55
<212> TYPE: DNA
<213> ORGANISM: Homo sapiens

<400> SEQUENCE: 91
ggcctctggg atttgggggt cacgcccgac ctctgggatt tgggggtcac gcccg         55
```

METHOD FOR THE ANALYSIS OF OVARIAN CANCER DISORDERS

FIELD OF THE INVENTION

The present invention is in the field of biology and chemistry, more in particular in the field of molecular biology and human genetics. The invention relates to the field of identifying methylated sites in human DNA, in particular methylated sites in certain defined sequences which when methylated are indicative of ovarian cancer.

BACKGROUND OF THE INVENTION

Ovarian cancer is the fifth leading cause of cancer death in women, the leading cause of death from gynecological malignancy, and the second most commonly diagnosed gynecologic malignancy (The Merck Manual of Diagnosis and Therapy Section 18. Gynecology And Obstetrics Chapter 241. Gynecologic Neoplasms).

It is idiopathic, meaning that the exact cause is usually unknown. The disease is more common in industrialized nations, with the exception of Japan. In the United States, females have a 1.4% to 2.5% (1 out of 40-60 women) lifetime chance of developing ovarian cancer.

More than half of the deaths from ovarian cancer occur in women between 55 and 74 years of age and approximately one quarter of ovarian cancer deaths occur in women between 35 and 54 years of age.

The risk for developing ovarian cancer appears to be affected by several factors.

The link to the use of fertility medication, such as clomiphene citrate, has been controversial. An analysis in 1991 raised the possibility that use of drugs may increase the risk for ovarian cancer. Several cohort studies and case-control studies have been conducted since then without providing conclusive evidence for such a link.

There is good evidence that genetic factors are important. Carriers of certain mutations of the BRCA1 or the BRCA2 gene, more frequent in some populations (e.g. Ashkenazi Jewish women) are at a higher risk of both breast cancer and ovarian cancer, often at an earlier age than the general population. Patients with a personal history of breast cancer or a family history of breast and/or ovarian cancer, especially if at a young age, may have an elevated risk. A strong family history of uterine cancer, colon cancer, or other gastrointestinal cancers may indicate the presence of a syndrome known as hereditary nonpolyposis colorectal cancer (HNPCC, also known as Lynch II syndrome), which confers a higher risk for developing ovarian cancer.

Other factors that have been investigated, such as talc use, asbestos exposure, high dietary fat content, and childhood mumps infection, are controversial and have not been definitively proven.

Ovarian cancer is classified according to the histology of the tumor (ICD-O codes). Histology dictates many aspects of clinical treatment, management, and prognosis.

Ovarian tumors can be classified by their presumed cell of origin. The main categories are, surface epithelial-stromal tumours, sex cord-stromal tumours (ICD-O 8590), germ cell tumours (ICD-O 9060-9090) and secondary or metastatic tumours.

Surface epithelial-stromal tumours are the most common and prototypic ovarian cancers. They are thought to originate from the ovarian surface lining, and include serous cystadenocarcinoma (8441/3), and mucinous cystadenocarcinoma (8470/3). The abdominal cavity is lined with the same cells that make up the ovarian surface lining, and it is possible to have cancer begin there, in which case, it is called primary peritoneal cancer. Treatment, however, is basically the same as treatment for ovarian cancer.

Sex cord-stromal tumors (8590) include lesions that are hormonally active such as the estrogen-producing granulosa cell tumor (8620/3) and the virilizing Sertoli-Leydig cell tumor or arrhenoblastoma.

Germ cell tumors (9060-9090) of the ovary originate from germ cells and tend to occur in young women and girls. These tumors represent approximately 5% of ovarian cancers. They tend to be well encapsulated and many are benign, hence prognosis than for other ovarian tumors.

There are also mixed tumors secondary or metastatic tumors.

Ovarian cancer often is primary, but can also be secondary, i.e. the result of metastasis from primary cancers elsewhere in the body, for example, from breast cancer, or from gastrointestinal cancer, in which case the ovarian cancer is a Krukenberg cancer.

Historically ovarian cancer was called the "silent killer" because symptoms were not thought to develop until the chance of cure was poor. However, recent studies have shown this term is untrue and that the following symptoms are much more likely to occur in women with ovarian cancer than women in the general population. These symptoms include, bloating, pelvic or abdominal pain, difficulty eating or feeling full quickly, urinary symptoms (urgency or frequency).

Early stage diagnosis is associated with an improved prognosis.

Several other symptoms have been commonly reported by women with ovarian cancer. These symptoms include fatigue, indigestion, back pain, pain with intercourse, constipation and menstrual irregularities. However, these other symptoms are not as useful in identifying ovarian cancer because they are also found in equal frequency in women in the general population who do not have ovarian cancer.

Ovarian cancer at its early stages (I/II) is difficult to diagnose until it spreads and advances to later stages (III/IV). This is due to the fact that most of the common symptoms are non-specific.

Ovarian cancer has a poor prognosis. It is disproportionately deadly because symptoms are vague and non-specific, hence diagnosis is late. More than 60% of patients presenting with this cancer already have stage III or stage IV cancer, when it has already spread beyond the ovaries.

Ovarian cancers that are malignant shed cells into the naturally occurring fluid within the abdominal cavity. These cells can implant on other abdominal (peritoneal) structures included the uterus, urinary bladder, bowel, lining of the bowel wall (omentum) and can even spread to the lungs. These cells can begin forming new tumor growths before cancer is even suspected.

More than 50% of women with ovarian cancer are diagnosed in the advanced stages of the disease because no cost-effective screening test for ovarian cancer exists. The five year survival rate for all stages is only 35% to 38%. If, however, diagnosis is made early in the disease, five-year survival rates can reach 90% to 98%.

Hence, it would be advantageous to have method for the analysis of ovarian cancer disorders as well as a method for detection of ovarian cancer in a subject.

SUMMARY OF THE INVENTION

The present invention teaches a method for the analysis of ovarian cancer disorders, comprising determining the genomic methylation status of one or more CpG dinucleotides in a sequence selected from the group of SEQ ID NO. 1 to 91 and/or determining the genomic methylation status of one or more CpG dinucleotides in particular of sequences according to SEQ ID NO. 1 to 10 and/or SEQ ID NO. 50 to SEQ ID NO. 60.

The regions of interest are designated in table 1A and table 1B ("start" and "end").

CpG islands are regions where there are a large number of cytosine and guanine adjacent to each other in the backbone of the DNA (i.e. linked by phosphodiester bonds). They are in and near approximately 40% of promoters of mammalian genes (about 70% in human promoters). The "p" in CpG notation refers to the phosphodiester bond between the cytosine and the guanine.

The length of a CpG island is typically 100-3000 base pairs. These regions are characterized by CpG dinucleotide content equal to or greater than what would be statistically expected ($\approx 6\%$), whereas the rest of the genome has much lower CpG frequency ($\approx 1\%$), a phenomenon called CG suppression. Unlike CpG sites in the coding region of a gene, in most instances, the CpG sites in the CpG islands of promoters are unmethylated if genes are expressed. This observation led to the speculation that methylation of CpG sites in the promoter of a gene may inhibit the expression of a gene. Methylation is central to imprinting alongside histone modifications. The usual formal definition of a CpG island is a region with at least 200 bp and with a GC percentage that is greater than 50% and with an observed/expected CpG ratio that is greater than 0.6.

Herein, a CpG dinucleotide is a CpG dinucleotide which may be found in methylated and unmethylated status in vivo, in particular in human.

The invention relates to a method, wherein a primary cancer is detected using the methylation pattern of one or more sequences disclosed herein and also, wherein the methylation pattern obtained is used to predict the therapeutic response to a treatment of an ovarian cancer.

Herein, a subject is understood to be all persons, patients, animals, irrespective whether or not they exhibit pathological changes. In the meaning of the invention, any sample collected from cells, tissues, organs, organisms or the like can be a sample of a patient to be diagnosed. In a preferred embodiment the patient according to the invention is a human. In a further preferred embodiment of the invention the patient is a human suspected to have a disease selected from the group of, primary ovarian cancer, secondary ovarian cancer, surface epithelial-stromal tumor, sex cord-stromal tumor, germ cell tumor.

The method is for use in the improved diagnosis, treatment and monitoring of ovarian cell proliferative disorders, for example by enabling the improved identification of and differentiation between subclasses of said disorder and the genetic predisposition to said disorders. The invention presents improvements over the state of the art in that it enables a highly specific classification of ovarian cell proliferative disorders, thereby allowing for improved and informed treatment of patients.

Herein, the sequences claimed also encompass the sequences which are reverse complement to the sequences designated.

DETAILED DESCRIPTION OF EMBODIMENTS

Figure 1:
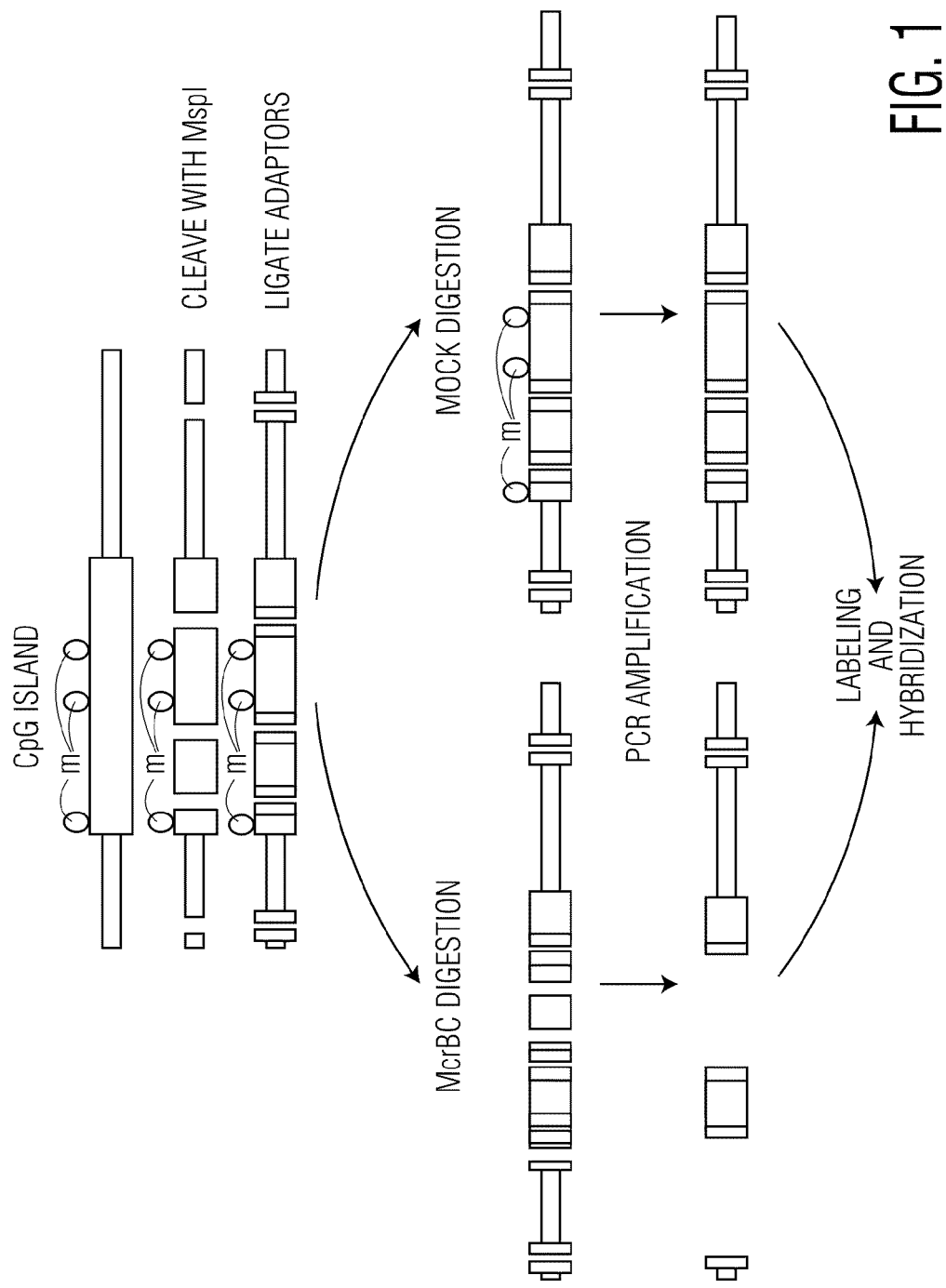
FIG. 1 shows the method for determination of differentially methylated regions of the genome. This is outlined in more detail in the Examples.
Figure 2:
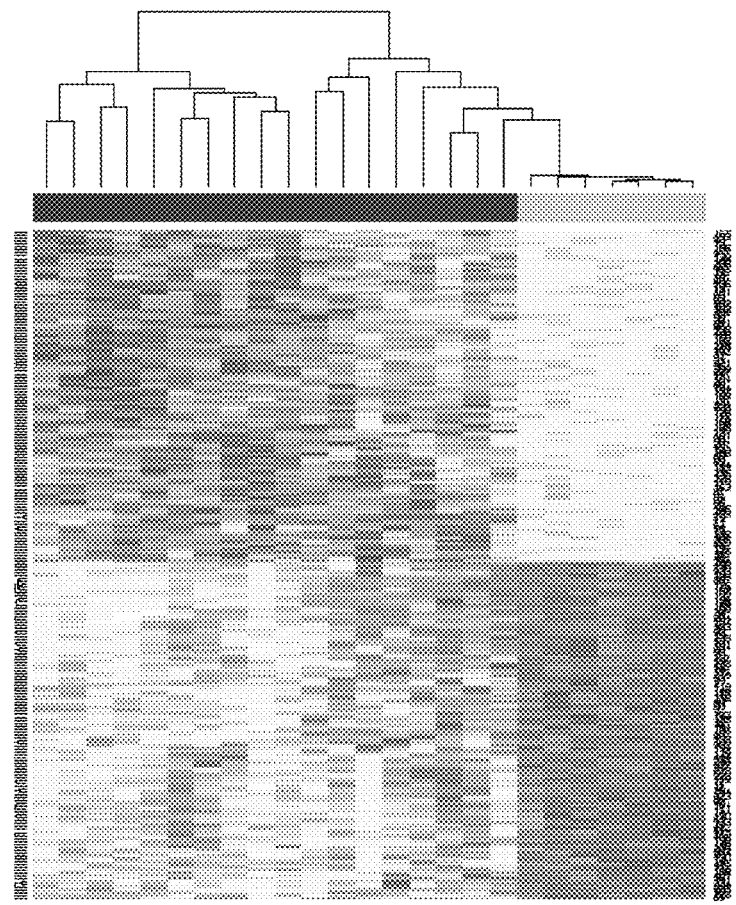
FIG. 2 shows clustered samples (columns) vs. methylation loci (rows). Methylation signatures can differentiate between tumors (left part of bar on top) and normal tissue (right part of bar on top).
Figure 3:
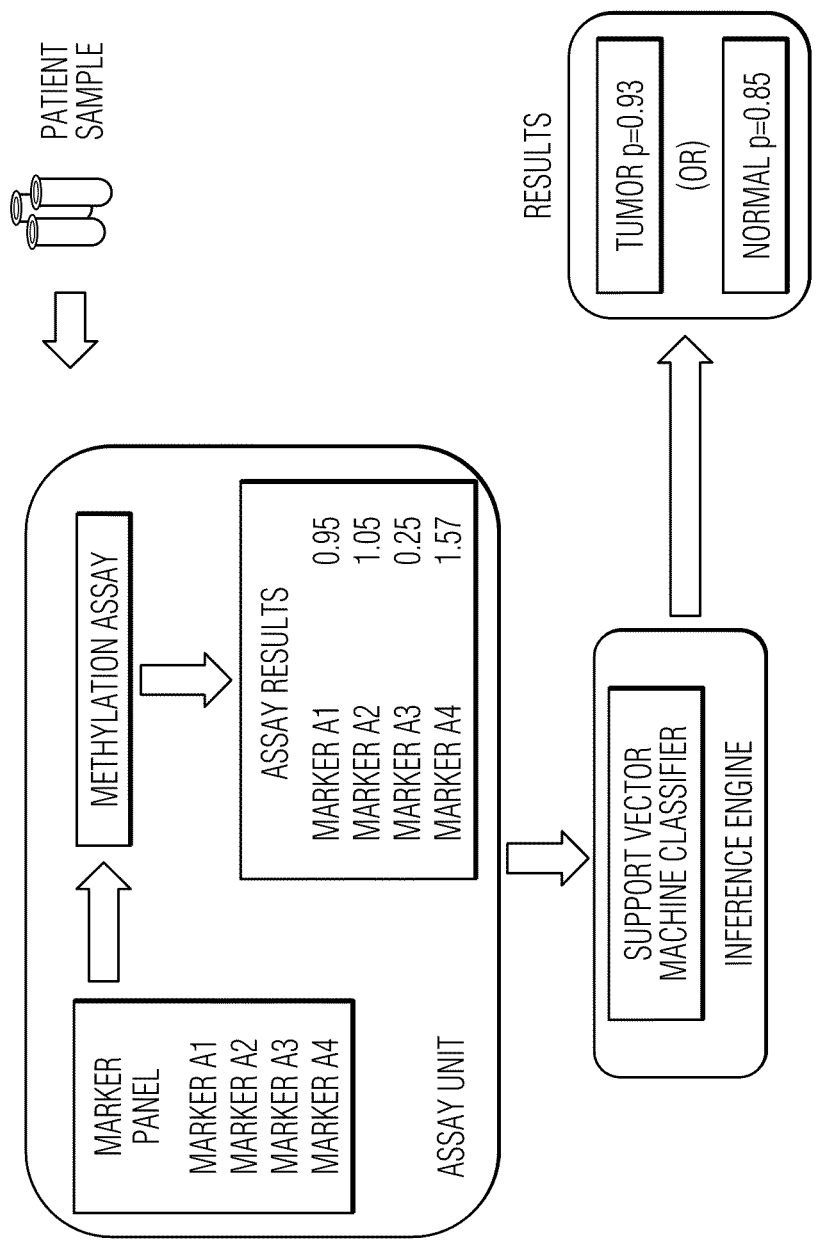
FIG. 3 shows a clustering of ovarian samples based on the methylation features. Unsupervised clustering can differentiate between normal and tumor samples.

The inventors have astonishingly found that a small selection of DNA sequences may be used to analyze ovarian cancer disorders. This is done by determining genomic methylation status of one or more CpG dinucleotides in either sequence disclosed herein or its reverse complement. About 900 sequences were identified in total that are suited for such an analysis. It turns out that 91 sequences are particularly suited.

Based on just 10 sequences, such as the first ten from table 1A or B (Pvalue 0.0001), it is possible to arrive at a classification accuracy for of 94%. The sequences may be found in genes as can be seen in table 1A below.

TABLE 1A

| SEQ ID NO. | ID | Chromosome | Start | End | P-val | Gene Promoter |
|---|---|---|---|---|---|---|
| 1 | ID88611 | chr19 | 5631787 | 5631904 | 0.0000315 | AY313896 |
| 2 | ID175860 | chr9 | 5440496 | 5442012 | 0.0000634 | BC069381 |
| 3 | ID83251 | chr18 | 42804624 | 42805591 | 0.0000758 | TCEB3C |
| 4 | ID123662 | chr22 | 46348054 | 46348410 | 0.0000952 | FLJ46257 |
| 5 | ID90252 | chr19 | 12706515 | 12706562 | 0.000100964 | ASNA1 |
| 6 | ID88853 | chr19 | 6410747 | 6411538 | 0.000109899 | CRB3 |
| 7 | ID106715 | chr2 | 1.53E+08 | 1.53E+08 | 0.000132458 | FMNL2 |
| 8 | ID76937 | chr17 | 45397876 | 45398117 | 0.000136 | DLX4 |
| 9 | ID22548 | chr10 | 1.01E+08 | 1.01E+08 | 0.000148441 | NKX2-3 |
| 10 | ID45743 | chr13 | 35818685 | 35818932 | 0.000157858 | SPG20 |
| 11 | ID106499 | chr2 | 1.39E+08 | 1.39E+08 | 0.000180479 | LOC339745 |
| 12 | ID131616 | chr3 | 1.63E+08 | 1.63E+08 | 0.000188374 | BC071875 |
| 13 | ID33153 | chr11 | 77528404 | 77528466 | 0.00021029 | ALG8 |
| 14 | ID69601 | chr16 | 88084505 | 88084566 | 0.000224742 | ANKRD11 |
| 15 | ID55562 | chr15 | 39412526 | 39412630 | 0.000231649 | OIP5 |
| 16 | ID82852 | chr18 | 31178284 | 31178321 | 0.00026884 | AF542097 |
| 17 | ID188098 | chrX | 1.14E+08 | 1.14E+08 | 0.000276279 | BC028688 |
| 18 | ID125695 | chr3 | 28365531 | 28365798 | 0.000277255 | AZI2 |
| 19 | ID69407 | chr16 | 87450852 | 87451117 | 0.000303853 | BC011369 |
| 20 | ID147776 | chr5 | 1.75E+08 | 1.75E+08 | 0.000354 | DRD1 |
| 21 | ID129197 | chr3 | 1.12E+08 | 1.12E+08 | 0.000378924 | BC067808 |

TABLE 1A-continued

| SEQ ID NO. | ID | Chromosome | Start | End | P-val | Gene Promoter |
|---|---|---|---|---|---|---|
| 22 | ID39382 | chr12 | 54509420 | 54509575 | 0.000415538 | AK057179 |
| 23 | ID138427 | chr4 | 1.21E+08 | 1.21E+08 | 0.00047605 | MAD2L1 |
| 24 | ID5570 | chr1 | 31752564 | 31752750 | 0.000526242 | HCRTR1 |
| 25 | ID120807 | chr22 | 23313706 | 23314029 | 0.000548859 | LOC388886 |
| 26 | ID175953 | chr9 | 6747544 | 6747604 | 0.000597361 | AB018323 |
| 27 | ID163464 | chr7 | 89868741 | 89869864 | 0.000623 | PFTK1 |
| 28 | ID119641 | chr22 | 17268168 | 17268417 | 0.000639985 | BC047039 |
| 29 | ID43355 | chr12 | 1.24E+08 | 1.24E+08 | 0.000681142 | BRI3BP |
| 30 | ID148329 | chr5 | 1.77E+08 | 1.77E+08 | 0.000707 | NY-REN-7 |
| 31 | ID178503 | chr9 | 88845701 | 88845932 | 0.000731649 | AK129921 |
| 32 | ID21652 | chr10 | 88717549 | 88718107 | 0.000744071 | C10orf116 |
| 33 | ID179700 | chr9 | 1.07E+08 | 1.07E+08 | 0.000767134 | RAD23B |
| 34 | ID77161 | chr17 | 46299407 | 46299451 | 0.000793328 | TOB1 |
| 35 | ID40416 | chr12 | 74712124 | 74712190 | 0.000802 | PHLDA1 |
| 36 | ID149652 | chr6 | 6572127 | 6575902 | 0.000808 | FLJ33708 |
| 37 | ID56526 | chr15 | 54812868 | 54813104 | 0.000829585 | SUHW4 |
| 38 | ID18295 | chr10 | 14960697 | 14960796 | 0.000868353 | SUV39H2 |
| 39 | ID68291 | chr16 | 82398697 | 82399030 | 0.000934789 | HSBP1 |
| 40 | ID51334 | chr14 | 72673142 | 72673174 | 0.000939 | PSEN1 |
| 41 | ID128265 | chr3 | 62836031 | 62836284 | 0.000954756 | CADPS |
| 42 | ID100401 | chr2 | 25387018 | 25387063 | 0.000974638 | DNMT3A |
| 43 | ID184276 | chrX | 550487 | 550772 | 0.00100771 | SHOX |
| 44 | ID2370 | chr1 | 7778659 | 7778715 | 0.001043041 | PER3 |
| 45 | ID34541 | chr11 | 1.18E+08 | 1.18E+08 | 0.001059334 | MIZF |
| 46 | ID78653 | chr17 | 68699787 | 68700038 | 0.001078955 | COG1 |
| 47 | ID55183 | chr15 | 35180110 | 35180409 | 0.001083766 | MEIS2 |
| 48 | ID160402 | chr7 | 27993506 | 27993623 | 0.00112 | JAZF1 |
| 49 | ID121081 | chr22 | 27793491 | 27793540 | 0.001117003 | BC063787 |

The sequences may also be found in intergenic regions as can be seen in table 1B below.

TABLE 1B

| SEQ ID NO. | ID | Chromosome | Start | End | P-val |
|---|---|---|---|---|---|
| 50 | ID89944 | chr19 | 10843569 | 10843613 | 0.0000227 |
| 51 | ID102184 | chr2 | 63152348 | 63153687 | 0.0000231 |
| 52 | ID28331 | chr11 | 27698553 | 27698834 | 0.0000338 |
| 53 | ID144851 | chr5 | 114908035 | 114908080 | 0.0000553 |
| 54 | ID128185 | chr3 | 58546910 | 58547629 | 0.00008 |
| 55 | ID93003 | chr19 | 40483018 | 40483245 | 0.000110513 |
| 56 | ID136801 | chr4 | 68239844 | 68239927 | 0.000144546 |
| 57 | ID146275 | chr5 | 140146252 | 140146717 | 0.000215464 |
| 58 | ID131177 | chr3 | 148621317 | 148621647 | 0.000216975 |
| 59 | ID12952 | chr1 | 158307786 | 158308067 | 0.000242093 |
| 60 | ID39999 | chr12 | 63439190 | 63439288 | 0.000286113 |
| 61 | ID116585 | chr20 | 61967316 | 61967544 | 0.000287984 |
| 62 | ID73971 | chr17 | 26742913 | 26742971 | 0.000311873 |
| 63 | ID125133 | chr3 | 13654044 | 13654318 | 0.000372628 |
| 64 | ID99092 | chr2 | 1654591 | 1654895 | 0.000372925 |
| 65 | ID69936 | chr16 | 88767910 | 88769082 | 0.000397396 |
| 66 | ID78601 | chr17 | 67623230 | 67623629 | 0.00041658 |
| 67 | ID148836 | chr5 | 179854129 | 179854384 | 0.000420579 |
| 68 | ID21285 | chr10 | 79714238 | 79714714 | 0.000425735 |
| 69 | ID158039 | chr7 | 922643 | 922835 | 0.000459 |
| 70 | ID32408 | chr11 | 70345916 | 70347923 | 0.000464267 |
| 71 | ID76532 | chr17 | 43973948 | 43974107 | 0.000501907 |
| 72 | ID178855 | chr9 | 93408533 | 93408596 | 0.0005196 |
| 73 | ID81125 | chr17 | 78514384 | 78516444 | 0.000559665 |
| 74 | ID100286 | chr2 | 24625709 | 24625843 | 0.000582927 |
| 75 | ID155118 | chr6 | 119711684 | 119711950 | 0.000636 |
| 76 | ID89463 | chr19 | 8668749 | 8668987 | 0.000646711 |
| 77 | ID9880 | chr1 | 94718230 | 94718935 | 0.000655989 |
| 78 | ID177108 | chr9 | 37016858 | 37016916 | 0.000661917 |
| 79 | ID68281 | chr16 | 81219051 | 81219377 | 0.000665387 |
| 80 | ID178263 | chr9 | 83765733 | 83765839 | 0.000669707 |
| 81 | ID34175 | chr11 | 113165828 | 113166488 | 0.00067498 |
| 82 | ID147847 | chr5 | 175420376 | 175420628 | 0.000688163 |
| 83 | ID47981 | chr13 | 111756373 | 111756614 | 0.000693087 |
| 84 | ID146308 | chr5 | 140181734 | 140181814 | 0.000694524 |
| 85 | ID17523 | chr10 | 1273925 | 1274241 | 0.00074504 |
| 86 | ID166673 | chr7 | 149355326 | 149355615 | 0.000762 |
| 87 | ID91016 | chr19 | 15399966 | 15400044 | 0.000779943 |
| 88 | ID101572 | chr2 | 45143519 | 45143913 | 0.000805715 |
| 89 | ID39294 | chr12 | 52897679 | 52898035 | 0.000854819 |
| 90 | ID50743 | chr14 | 61349222 | 61349293 | 0.00087795 |
| 91 | ID157888 | chr7 | 750241 | 750295 | 0.000912 |

The genes that form the basis of the present invention are preferably to be used to form a "gene panel", i.e. a collection comprising the particular genetic sequences of the present invention and/or their respective informative methylation sites. The formation of gene panels allows for a quick and specific analysis of specific aspects of ovarian cancer. The gene panel(s) as described and employed in this invention can be used with surprisingly high efficiency for the diagnosis, treatment and monitoring of and the analysis also of a predisposition to ovarian cell proliferative disorders in particular however to the detection of ovarian tumor.

In addition, the use of multiple CpG sites from a diverse array of genes allows for a relatively high degree of sensitivity and specificity in comparison to single gene diagnostic and detection tools.

The invention relates to a method for the analysis of ovarian cancer disorders, comprising determining the genomic methylation status of one or more CpG dinucleotides in a sequence selected from the group of sequences according to SEQ ID NO. 1 to SEQ ID NO. 10 and/or SEQ ID NO. 50 to SEQ ID NO. 60.

In one embodiment it is preferred that the methylation status of one or more of the sequences according to SEQ ID NO. 1 to 91 is determined, wherein the sequence has a p-value which is smaller than 0.0001 as designated in table 1A or 1B.

The methylation status of CpG islands is indicative of ovarian cancer. Preferably, however the methylation status is determined for each CpG and the differential methylation pattern is determined, because not all CpG islands necessarily need to be methylated.

In one embodiment of the method according to the invention the analysis is detection of ovarian cancer in a subject and wherein the following steps are performed, (a) providing a sample from a subject to be analyzed, (b) determining the methylation status of one or more CpG dinucleotides in a sequence selected from the group of sequences according to SEQ ID NO. 1 to SEQ ID NO. 10 and/or SEQ ID NO. 50 to SEQ ID NO. 60.

Optionally, additionally the following steps are performed, (a) the one or more results from the methylation status test is input into a classifier that is obtained from a Diagnostic Multi Variate Model, (b) the likelihood is calculated as to whether the sample is from a normal tissue or an ovarian cancer tissue and/or, (c) an associated p-value for the confidence in the prediction is calculated.

For example, we use a support vector machine classifier for "learning" the important features of a tumor or normal sample based on a pre-defined set of tissues from patients. The algorithm now outputs a classifier (an equation in which the variables are the methylation ratios from the set of features used). Methylation ratios from a new patient sample are then put into this classifier. The result can be 1 or 0. The distance from the marginal plane is used to provide the p-value.

It is preferred that the methylation status is determined for at least four of the sequences according to SEQ ID NO. 1 to 10 and/or SEQ ID NO. 50 to SEQ ID NO. 60.

It is preferred that additionally the methylation status is determined for one or more of the sequences according to SEQ ID NO. 11 to 49 and/or 61 to 91.

In one embodiment the methylation status is determined for at least ten sequences, twenty sequences, thirty sequences forty sequences or more than forty sequences of the sequences according to SEQ ID. NO. 1 to SEQ ID NO. 91. It is particularly preferred that the methylation status is determined for all of the sequences according to SEQ ID NO. 1 to SEQ ID NO. 91.

In one embodiment the methylation status is determined for the sequences according to SEQ ID. NO. 1 to SEQ ID NO. 10 and SEQ ID NO. 50 to SEQ ID NO. 60. In principle the invention also relates to determining the methylation status of only one of the sequences according to SEQ ID NO. 1 to SEQ ID NO. 91.

There are numerous methods for determining the methylation status of a DNA molecule. It is preferred that the methylation status is determined by means of one or more of the methods selected form the group of, bisulfite sequencing, pyrosequencing, methylation-sensitive single-strand conformation analysis (MS-SSCA), high resolution melting analysis (HRM), methylation-sensitive single nucleotide primer extension (MS-SnuPE), base-specific cleavage/MALDI-TOF, methylation-specific PCR (MSP), microarray-based methods, msp I cleavage. An overview of the further known methods of detecting 5-methylcytosine may be gathered from the following review article: Rein, T., DePamphilis, M. L., Zorbas, H., Nucleic Acids Res. 1998, 26, 2255. Further methods are disclosed in US 2006/0292564A1.

In a preferred embodiment the methylation status is determined by mspI cleavage, ligation of adaptors, McrBC digestion, PCR amplification, labeling and subsequent hybridization.

In a preferred embodiment the methylation status is determined as follows.

It is preferred that the sample to be analyzed is from a tissue type selected from the group of tissues such as, a tissue biopsy from the tissue to be analyzed, vaginal tissue, tongue, pancreas, liver, spleen, ovary, muscle, joint tissue, neural tissue, gastrointestinal tissue, tumor tissue, body fluids, blood, serum, saliva, and urine.

In a preferred embodiment a primary cancer is detected.

In one embodiment of the method according to the invention the methylation pattern obtained is used to predict the therapeutic response to the treatment of an ovarian cancer.

The invention relates to probes such as oligonucleotides which are in the region of up CpG sites. The oligomers according to the present invention are normally used in so called "sets" which contain at least one oligonucleotide for each of the CpG dinucleotides within SEQ ID NO. 1 through SEQ ID NO. 91 or at least for 10, preferred, 20, more preferred 30 most preferred more than 50 of said sequences. The invention also relates to the reverse complement of the oligonucleotides which are in the region of the CpG sites.

The probes to be used for such analysis are defined based on one or more of the following criteria: (1) Probe sequence occurs only once in the human genome; (2) Probe density of C/G nucleotides is between 30% and 70%; (3) Melting characteristics of hybridization and other criteria are according to Mei R et al, *Proc Natl Acad Sci USA*. 2003 Sep. 30; 100(20): 11237-42.

In a very preferred embodiment the mention relates to a set of oligonucleotides, which are specific for the sequences according to SEQ ID NO. 1 to 10 and/or SEQ ID NO: 50 to 60, or SEQ ID NO. 50 to 60. The oligonucleotide according to the invention may be specific for the sequence as it occurs in vivo or it may be specific for a sequence which has been bisulfite treated. Such a probe is between 10 and 80 nucleotides long, more preferred between 15 and 40 nucleotides long.

In the case of the sets of oligonucleotides according to the present invention, it is preferred that at least one oligonucleotide is bound to a solid phase. It is further preferred that all the oligonucleotides of one set are bound to a solid phase.

The present invention further relates to a set of at least 10 probes (oligonucleotides and/or PNA-oligomers) used for detecting the cytosine methylation state of genomic DNA, by analysis of said sequence or treated versions of said sequence (according to SEQ ID NO. 1 through SEQ ID NO. 91 and sequences complementary thereto).

These probes enable improved detection, diagnosis, treatment and monitoring of ovarian cell proliferative disorders.

The set of oligonucleotides may also be used for detecting single nucleotide polymorphisms (SNPs) by analysis of said sequence or treated versions of said sequence according to one of SEQ ID NO. 1 through SEQ ID NO. 91.

According to the present invention, it is preferred that an arrangement of different oligonucleotides and/or PNA-oligomers (a so-called "array") made available by the present invention is present in a manner that it is likewise bound to a solid phase.

This array of different oligonucleotide- and/or PNA-oligomer sequences can be characterised in that it is arranged on the solid phase in the form of a rectangular or hexagonal lattice. The solid phase surface is preferably composed of silicon, glass, polystyrene, aluminium, steel, iron, copper, nickel, silver, or gold. However, nitrocellulose as well as plastics, such as nylon which can exist in the form of pellets or also as resin matrices, are suitable alternatives.

Therefore, a further subject matter of the present invention is a method for manufacturing an array fixed to a carrier material for the improved detection, diagnosis, treatment and monitoring of ovarian cell proliferative disorders and/or detection of the predisposition to ovarian cell proliferative disorders. In said method at least one oligonucleotide according to the present invention is coupled to a solid phase. Methods for manufacturing such arrays are known, for example, from U.S. Pat. No. 5,744,305 by means of solid-phase chemistry and photolabile protecting groups. A further subject matter of the present invention relates to a DNA chip for the improved detection, diagnosis, treatment and monitoring of ovarian cell proliferative disorders. Furthermore, the DNA chip enables detection of the predisposition to ovarian cell proliferative disorders.

The DNA chip contains at least one nucleic acid and/or oligonucleotide according to the present invention. DNA-chips are known, for example, in U.S. Pat. No. 5,837,832.

The invention relates to a composition or array comprising nucleic acids with sequences which are identical to at least 10 of the sequences according to SEQ ID NO. 1 to 91, wherein the composition or array comprises no more than 100 different nucleic acid molecules.

The present invention relates to a composition or array comprising at least 5 sequences with a cumulative p-value of under 0.001, preferred under 0.0001.

Moreover, a subject matter of the present invention is a kit which may be composed, for example, of a bisulfitecontaining reagent, a set of primer oligonucleotides containing at least two oligonucleotides whose sequences in each case correspond to or are complementary to an at least 15 base long segment of the base sequences specified in SEQ ID NO. 1 to SEQ ID NO. 91. It is preferred that the primers are for SEQ ID NO. 1 through 10 and/or SEQ ID NO. 50 through SEQ ID NO. 60.

EXAMPLES

Samples

Patient samples were obtained from Norwegian Radium Hospital, Oslo, Norway and patient consent obtained as per legal requirements.

CpG Islands

Annotated CpG islands were obtained from the UCSC genome browser. These islands were predicted using the published Gardiner-Garden definition (Gardiner-Garden, M. and M. Frommer (1987). "CpG islands in vertebrate genomes." J Mol Biol 196(2): 261-82) involving the following criteria: length >=200 bp, % GC>=50%, observed/expected CpG >=0.6. There are ~26219 CpG islands in the range of 200 bp to 2000 bp in the genome. These islands are well covered by Msp I restriction fragmentation.

Arrays were manufactured by Nimblegen Systems Inc using the 390K format to the following specifications. The CpG island annotation from human genome build 33 (hg17) was used to design a 50 mer tiling array. The 50 mers were shifted on either side of the island sequence coordinates to evenly distribute the island. The 390K format has 367,658 available features which would not fit all islands with a 50 mer tiling. Therefore we made a cutoff on the islands to be represented based on size, with only CpG islands of size 200b-2000b being assayed. Control probes were designed to represent background signal. Sample preparation: representations, has been described previously (Lucito, R., J. Healy, et al. (2003). "Representational oligonucleotide microarray analysis: a high-resolution method to detect genome copy number variation." Genome Res 13(10): 2291-305.), with the following changes. The primary restriction endonuclease used is MspI. After the digestion the following linkers were ligated (MspI24mer, and MSPI12mer). The 12 mer is not phosphorylated and does not ligate. After ligation the material is cleaned by phenol chloroform, precipitated, centrifuged, and re-suspended. The material is divided in two, half being digested by the endonuclease McrBC and the other half being mock digested. As few as four 2500 tubes were used for each sample pair for amplification of the representation each with a 100 ul volume reaction. The cycle conditions were 95° C. for 1 min, 72° C. for 3 min, for 15 cycles, followed by a 10-min extension at 72° C. The contents of the tubes for each pair were pooled when completed. Representations were cleaned by phenol:chloroform extraction, precipitated, resuspended, and the concentration determined. DNA was labeled as described with minor changes (Lucito, R., J. Healy, et al. (2003). "Representational oligonucleotide microarray analysis: a high-resolution method to detect genome copy number variation." Genome Res 13(10): 2291-305.). Briefly, 2 ug of DNA template was placed (dissolved in TE at pH 8) in a 0.2 mL PCR tube. 5 μl of random nonomers (Sigma Genosys) were added brought up to 25 μL with dH2O, and mixed. The tubes were placed in Tetrad at 100° C. for 5 min, then on ice for 5 min. To this 5 μl of NEB Buffer2, 5 μL of dNTPs (0.6 nm dCTP, 1.2 nm dATP, dTTP, dGTP), 5 μl of label (Cy3-dCTP or Cy5-dCTP) from GE Healthcare, 2 μl of NEB Klenow fragment, and 2 μl dH2O was added. Procedures for hybridization and washing were followed as reported previously (Lucito, R., J. Healy, et al. (2003). "Representational oligonucleotide microarray analysis: a high-resolution method to detect genome copy number variation." Genome Res 13(10): 2291-305) with the exception that oven temperature for hybridization was increased to 50° C. Arrays were scanned with an Axon GenePix 4000B scanner set at a pixel size of 5 μm. GenePix Pro 4.0 software was used to quantify the intensity for the arrays. Array data were imported into S-PLUS for further analysis.

Data Analysis

Microarray images were scanned on GenePix 4000B scanner and data extracted using Nimblescan software (Nimblegen Systems Inc). For each probe, the geometric mean of the ratios (GeoMeanRatio) of McrBc and control treated samples were calculated for each experiment and its associated dye swap. The GeoMeanRatios of all the samples in a dataset were then normalized using quantile normalization method (Bolstad, B. M., R. A. Irizarry, et al. (2003). "A comparison of normalization methods for high density oligonucleotide array data based on variance and bias" Bioinformatics 19(2): 185-93). The normalized ratios for each experiment were then collapsed to get one value for all probes in every MspI fragment using a median polish model. The collapsed data was then used for further analysis.

Analysis of variance was used to identify the most significant islands. In order to determine the most consistently occurring changes in methylation between tumor and normal samples, we used a t-test approach. Using a p-value cutoff of 0.001 after correction for multiple testing (False Discovery Rate, Benjamini and Hotchberg (Benjamini 1995)), we obtained a list of 916 MspI fragments that show differential methylation Supervised learning: We used a supervised machine learning classifier to identify the number of features required to differentiate tumor samples from normal. A publicly available support vector machine (SVM) library (LibSVM Ver 2.8) was used to obtain classification accuracy using a leave one out method (Lin, C.-C. C. a. C.-J. (2001). LIBSVM: a library for support vector machines). The methylation features for classification were first selected using t-test among the training data alone. The SVM was then trained on the top 10, 50 and 100 features using the radial basis function (RBF) kernel.

For N samples, t-tests were performed for (N−1) samples to identify fragments with significant differences in methylation ratios. For the ovarian dataset this was performed 18 times for all 18 ovarian samples, so that each sample is left out once during the t-test calculations. The methylation ratios of top 10 fragment features from (N−1) samples were then used for training the SVM and the ratios from one untrained sample was used for testing. Based on just 10 features, we can arrive at a classification accuracy of 94%. Interestingly the two tumor samples that were classified as normal in this analysis were also the closest to normal in both gene expression and ROMA analysis.

Detection of Methylated Sites

In a preferred embodiment, the method comprises the following steps: In the first step of the method the genomic DNA sample must be isolated from sources such as cell lines, tissue or blood samples. Extraction may be by means that are standard to one skilled in the art these include the use of detergent lysates, sonification and vortexing with glass beads. Once the nucleic acids have been extracted the genomic double stranded DNA is used in the analysis.

In a preferred embodiment the DNA may be cleaved prior to the next step of the method, this may by any means standard in the state of the art, in particular, but not limited to, with restriction endonucleases.

In the second step of the method, the genomic DNA sample is treated in such a manner that cytosine bases which are unmethylated at the 5'-position are converted to uracil, thymine, or another base which is dissimilar to cytosine in terms of hybridisation behaviour. This will be understood as 'pretreatment' hereinafter.

The above described treatment of genomic DNA is preferably carried out with bisulfite (sulfite, disulfite) and subsequent alkaline hydrolysis which results in a conversion of non-methylated cytosine nucleobases to uracil or to another base which is dissimilar to cytosine in terms of base vairine behaviour. If bisulfite solution is used for the reaction, then an addition takes place at the non-methylated cytosine bases. Moreover, a denaturating reagent or solvent as well as a radical interceptor must be present. A subsequent alkaline hydrolysis then gives rise to the conversion of non-methylated cytosine nucleobases to uracil. The converted DNA is then used for the detection of methylated cytosines.

Fragments are amplified. Because of statistical and practical considerations, preferably more than ten different fragments having a length of 100-2000 base pairs are amplified. The amplification of several DNA segments can be carried out simultaneously in one and the same reaction vessel. Usually, the amplification is carried out by means of a polymerase chain reaction (PCR). The design of such primers is obvious to one skilled in the art. These should include at least two oligonucleotides whose sequences are each reverse complementary or identical to an at least 15 base-pair long segment of the base sequences specified in the appendix (SEQ ID NO. 1 through SEQ ID NO. 91). Said primer oligonucleotides are preferably characterised in that they do not contain any CpG dinucleotides. In a particularly preferred embodiment of the method, the sequence of said primer oligonucleotides are designed so as to selectively anneal to and amplify, only the ovarian cell specific DNA of interest, thereby minimising the amplification of background or non relevant DNA. In the context of the present invention, background DNA is taken to mean genomic DNA which does not have a relevant tissue specific methylation pattern, in this case, the relevant tissue being ovarian cells, both healthy and diseased.

According to the present invention, it is preferred that at least one primer oligonucleotide is bound to a solid phase during amplification. The different oligonucleotide and/or PNA-oligomer sequences can be arranged on a plane solid phase in the form of a rectangular or hexagonal lattice, the solid phase surface preferably being composed of silicon, glass, polystyrene, aluminium, steel, iron, copper, nickel, silver, or gold, it being possible for other materials such as nitrocellulose or plastics to be used as well. The fragments obtained by means of the amplification may carry a directly or indirectly detectable label. Preferred are labels in the form of fluorescence labels, radionuclides, or detachable molecule fragments having a typical mass which can be detected in a mass spectrometer, it being preferred that the fragments that are produced have a single positive or negative net charge for better detectability in the mass spectrometer. The detection may be carried out and visualized by means of matrix assisted laser desorptiodionisation mass spectrometry (MALDI) or using electron Spray mass spectrometry (ESI).

In the next step the nucleic acid amplicons are analyzed in order to determine the methylation status of the genomic DNA prior to treatment.

The post treatment analysis of the nucleic acids may be carried out using alternative methods. Several methods for the methylation status specific analysis of the treated nucleic acids are known, other alternative methods will be obvious to one skilled in the art.

Using several methods known in the art the analysis may be carried out during the amplification step of the method. In one such embodiment, the methylation status of preselected CpG positions within the nucleic acids comprising SEQ ID NO. 1 through SEQ ID NO. 91 may be detected by use of methylation specific primer oligonucleotides. This technique has been described in U.S. Pat. No. 6,265,171.

The invention claimed is:

1. A method for analyzing methylation status in a human subject, comprising:
   providing a sample from the subject;
   determining a genomic methylation status of CpG dinucteotides in DNA from the subject, the DNA including sequences consisting of SEQ ID NO. 1 to SEQ ID NO. 10;
   wherein the methylation status is determined by means of at least one of the methods selected from the group of:
   bisulfite sequencing;
   pyrosequencing;
   methylation-sensitive single-strand conformation analysis (MS-SSCA);
   high resolution melting analysis (HRM);
   methylation-sensitive single nucleotide primer extension (MS-SnuPE);
   base-specific cleavage/MALDI-TOF;
   methylation-specific PCR (MSP);
   microarray-based methods; and
   msp I cleavage.

2. The method according to claim 1, wherein the methylation status is further determined in DNA sequences consisting of SEQ ID NO. 50 to SEQ ID NO. 60.

3. The method according to claim 1, wherein the methylation status is further determined in DNA sequences consisting of at least one of SEQ ID NO. 11 to 49 and SEQ ID NO. 61 to 91.

4. The method according to claim 1, wherein the sample to be analyzed is from a tissue type selected from the group of tissues:
   a tissue biopsy from the tissue to be analyzed, vaginal tissue, tongue, pancreas, liver, spleen, ovary, muscle, joint tissue, neural tissue, gastrointestinal tissue, tumor tissue, body fluids, blood, serum, saliva and urine.

* * * * *